US006232467B1

(12) United States Patent
Petasis et al.

(10) Patent No.: US 6,232,467 B1
(45) Date of Patent: May 15, 2001

(54) METHOD FOR THE SYNTHESIS OF AMINES AND AMINO ACIDS WITH ORGANOBORON DERIVATIVES

(75) Inventors: Nicos A. Petasis, Hacienda Heights; Ilia A. Zavialov, S. Pasadena, both of CA (US)

(73) Assignee: University of Southern California, University Park, CA (US)

( * ) Notice: Subject to any disclaimer, the term of this patent is extended or adjusted under 35 U.S.C. 154(b) by 0 days.

(21) Appl. No.: 08/884,188

(22) Filed: Jun. 27, 1997

Related U.S. Application Data
(60) Provisional application No. 60/020,741, filed on Jun. 28, 1996.

(51) Int. Cl.[7] .................... C07C 209/00; C07C 209/24
(52) U.S. Cl. .................... 544/171; 548/532; 548/533; 549/58; 549/75; 549/76; 549/480; 560/29; 562/441; 562/443; 562/444; 562/450; 562/457; 564/321; 564/355; 564/384; 564/389; 564/391; 564/471
(58) Field of Search .................... 544/171; 548/532, 548/533; 549/58, 75, 76, 480; 560/29; 562/441, 443, 444, 450, 457; 564/471, 321, 355, 384, 389, 391

(56) References Cited

FOREIGN PATENT DOCUMENTS 0 736 509 A2   10/1996   (EP) .

OTHER PUBLICATIONS

O'Donnell, Martin J., et al., "The Synthesis of Amino Acids via Organoboranes." J. Chem, Soc., Chem. Commun., pp. 1168–1169, 1985.

Petasis, Nicos A., et al., "The Boronic Acid Mannich Reaction: A New Method for the Synthesis of Geometrically Pure Allylamines." Tetrahedron Letters, vol. 34, No. 4, pp. 583–586, 1993.

Petasis, Nicos, A., et al., "A New and Practical Synthesis of a–Amino Acids from Alkenyl Boronic Acids." J. Am. Chem. Soc., vol. 119, No. 2, pp. 445–446, 1997.

Yamamoto, Yoshinori, et al., "Selective Reactions Using Allylic Metals." Chem. Rev., vol. 93, pp. 2207–2293, 1993.

*Primary Examiner*—Richard L. Raymond
(74) *Attorney, Agent, or Firm*—Fish & Richardson P.C.

(57) ABSTRACT

Amines and amino acids are prepared by reacting an amine, a carbonyl derivative, and an organoboron compound under mild conditions.

21 Claims, No Drawings

METHOD FOR THE SYNTHESIS OF AMINES AND AMINO ACIDS WITH ORGANOBORON DERIVATIVES

CROSS REFERENCE TO RELATED APPLICATIONS

This application is based on and claims the benefit under 35 U.S.C. §119 (e) of U.S. provisional application serial No. 60/020,741, filed Jun. 28, 1996, incorporated herein by reference in full.

FIELD OF THE INVENTION

This invention relates to the fields of organic synthesis, organoboron chemistry, medicinal chemistry and combinatorial chemistry. More specifically, the invention relates to methods for preparing amines and amino acids using organoboron compounds.

BACKGROUND OF THE INVENTION

A variety of amines and amino acids (1–8) are of particular interest for the preparation of many types of compounds that are of interest to chemical, agrochemical, biotechnology and pharmaceutical industries. In particular there is a need for a method which allows the production of novel combinatorial libraries of amines and amino acids and is also suitable for the large scale preparation of such compounds.

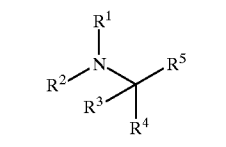

1

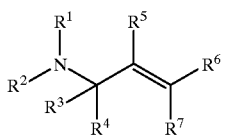

2

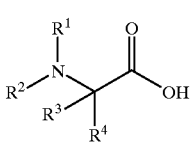

3

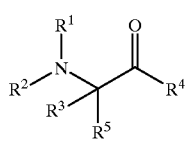

4

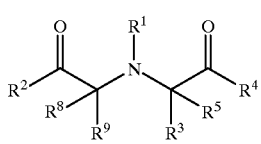

5

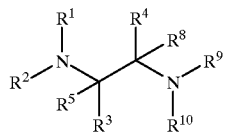

6

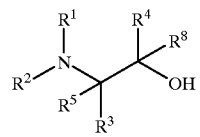

7

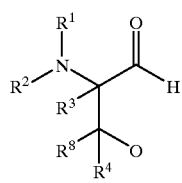

8

α-Amino acids (3) constitute a major class of naturally occurring molecules and have important and diverse biological functions. (G. C. Barrett, Ed., "Chemistry and Biochemistry of the Amino Acids", Chapman and Hall, London, (1985)). Nearly a thousand naturally occurring amino acids are known and their number is constantly increasing. Besides their profound biological role as constituents of proteins, amino acids have been extensively used in organic synthesis as convenient and versatile precursors to many other target molecules.

Although there are many known methods for the synthesis of amino acids (R. M. Williams, "Synthesis of Optically Active α-Amino Acids", Pergamon Press, Oxford, (1989); R. M. Williams, Aldrichim. Acta (1992) 25:11; R. O. Duthaler, Tetrahedron (1994) 50:1539), most of these have a number of drawbacks including the use of toxic or hazardous reagents, the need for anhydrous or anaerobic conditions, the cumbersome isolation procedures, the requirement for multiple reaction steps, the limited applicability to certain substitution patterns, and difficulty in controling stereochemistry or isomeric purity.

In addition to the need to develop practical synthetic routes to the natural amino acids, for which there is a large and growing market, there is also an increasing demand for new methods to prepare diverse non-natural derivatives. Such compounds can serve as building blocks in combinatorial peptide synthesis and for the development of enzyme inhibitors, peptidomimetics and other bioactive molecules (G. M. Coppola and H. F. Schuster, "Asymmetric Synthesis: Construction of Chiral Molecules Using Amino Acids", Wiley-Interscience, New York, (1987)). Amino acids with unusual side chains or with conformationally restricted backbones are of great interest due to their potential ability for highly selective receptor binding.

The valuable role of amines and amino acids in a variety of commercial applications requires practical and efficient methods for their preparation. This type of synthetic technology should have two important features, both of which are characteristic of the present invention: At the research and development stage, it is highly desirable to employ methods that allow the rapid production of a diverse array of molecules having many types of structural modifications, allowing the facile preparation of combinatorial libraries. Also, once a commercial product is identified, the required methodology for its large scale preparation should be characterized by high efficiency, low cost, facile isolation and purification, and low environmental hazards.

Known methods of multicomponent synthesis include the Strecker amino acid synthesis which involves the addition of cyanide to the adduct of a carbonyl compound and an amine to form aminonitriles, which can be hydrolyzed to amino acids. Another related method is the Ugi multicomponent reaction (I. Ugi et al. *Endeavour* (1994) 18:115), which involves the use of isonitriles for the formation of adducts which can be hydrolyzed to peptide derivatives.

The use of organoboron derivatives for the synthesis of substituted amines and amino acids in a multicomponent fashion as described herein, has no precedent in the literature. Although I have previously reported preliminary results on the use of (E)-alkenyl boronic acids for the synthesis of (E)-allylamines from amines and paraformaldehyde (N. A. Petasis et al., *Tetrahedron Lett.* (1993) 34:583), this initial stepwise procedure involves high temperatures and rather harsh conditions which are quite limited in scope due to the decomposition of the starting materials and intermediates. Thus, while the reported method can be used for the preparation of simple allylamines, it is not suitable for the synthesis of more substituted allylamines or amino acids, which have to be derived from aldehydes and ketones other than paraformaldehyde, or from other types of boronic acids.

From the mechanistic point of view, the chemistry covered by this invention resembles a boron-directed Mannich reaction. While the conventional Mannich reaction is known (E. F. Kleinman et al., *Comprehensive Organic Synthesis* (1991) 4:893; H. Heaney, *Comprehensive Organic Synthesis* (1991) 4:953; M. Tramontini and L. Angiolini, "Mannich Bases: Chemistry and Uses", CRC Press, Boca Raton, (1994)), the use of relatively stable organoboron compounds to deliver various organic groups in a directed and stereo-controlled manner is not reported. The only types of boron-based reagents that are known to add to imines are the highly reactive allylic boranes and allylic boronates (W. R. Roush, *Comprehensive Organic Synthesis* (1991) 2:1; E. F. Kleinman et al., *Comprehensive Organic Synthesis* (1991) 4:975; Y. Yamamoto et al., *Chem. Rev.* (1993) 93:2207). However, despite an apparent similarity among allylic organoboron compounds with the corresponding alkenyl, aryl or alkyl derivatives, there is a significant difference in their reactivity. Thus, the "Grignard-like" addition of allylic nucleophiles to carbonyl-derived electrophiles involves a cyclic six-membered transition state. This mode of action, however, is not possible with other organoboron compounds, such as the ones utilized herein.

Among the compounds of interest are β,γ-unsaturated-α-amino acids (3, $R^3$ or $R^4$=alkenyl), which have found numerous applications as synthetic intermediates and as mechanism-based suicide enzyme inhibitors, particularly of enzymes that metabolize amino acids, such as decarboxylases, transaminases or aminotransferases (L. Havlicek et al., *Collect. Czech. Chem. Commun.* (1991) 56:1365).

Another important class of amino acids is the aryl glycines (3, $R^3$ or $R^4$=aryl), which is found in many glycoptide and β-lactam antibiotics (R. M. Williams et al., *Chem. Rev.* (1992) 92:889). The synthesis of such amino acids by other methods is often hampered by their facile epimerization and the difficulty to control stereochemistry and isomerism.

N-carboxymethyl amino acid or peptide derivatives, i.e. compounds of the general formula 5, are especially valuable as peptidomimetics and have been used in several enzyme inhibitors (C. J. Blankley et al., *J. Med. Chem.* (1987) 30:992; J. Krapcho et al., *J. Med. Chem.* (1988) 31:1148). Among the most notable is enalaprilat 9 (the active ingredient in the drug vasotec) and lisinopril (10), which are potent inhibitors of angiotensin-converting enzyme (ACE) used clinically for the treatment of hypertension (I. M. Wilde et al., *Pharmaeconomics* (1994) 6:155). Similar compounds have also been considered as inhibitors of metalloproteinases (K. Chapman et al., *J. Med. Chem.* (1993) 36:4293) with a potential use against cancer, arthritis and other diseases.

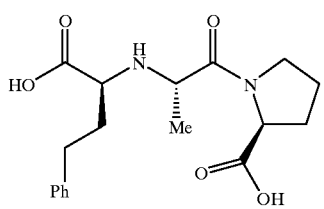

9

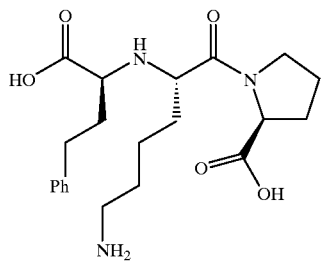

10

Other compounds of ineterest include substituted amines (1) and particularly allylic or benzylic amines (2), 1,2-diamines (6), 1,2-amino alcohols (7) and α-amino aldehyde derivatives (8), all of which are very common components of a variety of bioactive molecules, including inhibitors of proteases and other enzymes, which are used as pharmaceuticals or agrochemicals. Among the compounds of the general formula 8 are those having additional hydroxyl groups within $R^4$ or $R^8$ which include various amino sugar derivatives (R. W. Jeanloz, "The Amino Sugars", Academic Press, New York, (1969) exemplified by 11 and 12.

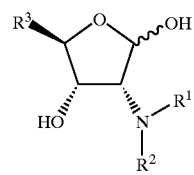

11

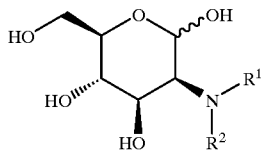

12

SUMMARY OF THE INVENTION

I have now invented a practical and effective method for the synthesis of various amines and amino acids by combining certain organoboron derivatives, including organoboronic acids, organoboronates and organoborates with primary or secondary amines and carbonyl compounds. This process constitutes a 3-component reaction and is suitable for the rapid generation of combinatorial libraries of amines, amino acids and peptidomimetic components.

The synthetic procedure is quite simple and works in a variety of solvents, including water, ethanol, dichloromethane and toluene. Product isolation is also very simple and can give fairly pure products without the need for chromatography or distillation. Of special significance is the fact that this process generates new C—C bonds with very high stereoselectivity (up to more than 99% de and 99% ee) when certain chiral components are used in the reaction. Due to its operational simplicity and the fact that no hazardous chemicals or special precautions are required, this invention is suitable for the practical and convenient synthesis of many types of amines and amino acids, including stereochemically pure derivatives. In this manner, this invention is useful for the preparation of various pharmaceuticals and agrochemicals.

One aspect of the invention is a process for generating substituted amines and amino acids, by reacting an organoboron compound with a carbonyl derivative and an amine under mild conditions.

Another aspect of the invention is a process for generating a combinatorial library of amines, amino acids, or amino acid mimics, by reacting an organoboron compound with a carbonyl derivative and an amine under mild conditions.

Another aspect of the invention is a combinatorial library generated through the process of the invention. The invention offers unique opportunities for the one-step introduction of a diverse group of functional groups in a variety of locations on the molecules produced, located in up to 8 substituent groups.

DESCRIPTION OF THE PREFERRED EMBODIMENTS

Definitions:

An organoboron derivative, as defined herein, comprises a compound having a boron atom connected to at least one alkyl, alkenyl, aryl, allenyl or alkynyl group.

Alkyl groups of the present invention include straight-chained, branched and cyclic alkyl radicals containing up to about 20 carbons. Suitable alkyl groups may be saturated or unsaturated. Further, an alkyl may also be substituted one or more times on one or more carbons with substituents selected from the group consisting of C1–C6 alkyl, C3–C6 heterocycle, aryl, halo, hydroxy, amino, alkoxy and sulfonyl. Additionally, an alkyl group may contain up to 10 heteroatoms. Suitable heteroatoms include nitrogen, oxygen and sulfur.

Aryl groups of the present invention include aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

The term "combinatorial library" as used herein refers to a set of compounds that are made by the same process, by varying one or more of the reagents. Combinatorial libraries may be made as mixtures of compounds, or as individual pure compounds, generally depending on the methods used for identifying active compounds. Where the active compound may be easily identified and distinguished from other compounds present by physical and/or chemical characteristics, it may be preferred to provide the library as a large mixture of compounds. Large combinatorial libraries may also be prepared by massively parallel synthesis of individual compounds, in which case compounds are typically identified by their position within an array. Intermediate between these two strategies is "deconvolution", in which the library is prepared as a set of sub-pools, each having a known element and a random element. For example, using the process of the invention each sub-pool might be prepared from only a single amine (where each sub-pool contains a different amine), but a mixture of different carbonyl derivatives (or organoboron reagents). When a sub-pool is identified as having activity, it is resynthesized as a set of individual compounds (each compound having been present in the original active sub-pool), and tested again to identify the compounds responsible for the activity of the sub-pool.

General Description:

This invention involves the use of organoboron compounds in a C—C bond forming reaction where the electrophile is derived from a carbonyl and an amine and the product is a new substituted amine or amino acid. There are several variations of this methodology involving different organoboron, carbonyl and amine components:

Synthesis of amines: One aspect of the invention is a process for generating a combinatorial library consisting of compounds of formula 1, by combining compounds 13, 14 and 15:

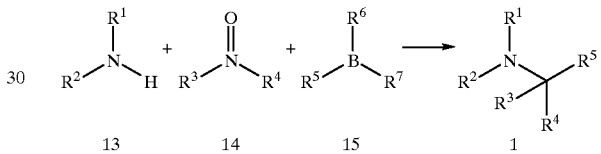

where $R^1$ and $R^2$ are each independently selected from the group consisting of alkyl, hydrogen, cycloalkyl, aryl, heteroaryl, acyl, carboxy, carboxamido, trialkylsilyl, aryldialkylsilyl, diarylalkylsilyl, triarylsilyl, phosphinyl, and —YR, where Y is selected from the group consisting of —O—, —NR$_a$—, —S—, —SO—, and —SO$_2$—, and R and R$_a$ are each independently selected from the group consisting of hydrogen, alkyl, aryl, heteroaryl, and acyl, or $R^1$ and $R^2$ together form a methylene bridge of 2 to 20 carbon atoms; and where $R^3$ and $R^4$ are each independently selected from the group consisting of hydrogen, hydroxy, alkoxy, aryloxy, heteroaryloxy, carboxy, amino, alkylamino, dialkylamino, acylamino, carboxamido, thio, alkylthio, arylthio, acylthio, alkyl, cycloalkyl, aryl, and heteroaryl; and where $R^5$ is selected from the group consisting of alkyl, cycloalkyl, aryl, heteroaryl, alkenyl, alkynyl and allenyl; $R^6$, $R^7$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms.

Following their formation, the products of the invention (1) can be subsequently easily transformed to new derivatives. For example, removing groups $R^1$ and $R^2$ can provide primary amines, while joining two or more groups will result in the formation of cyclic or polycyclic amines.

The multicomponent nature of the process described in this invention allows the direct and rapid generation of combinatorial libraries of the products, by varying the desired substituents. Such libraries can be generated either in solution or in the solid phase, upon attachment of one substituent onto a solid support. For example, one may couple the amine component (13) to a substrate through either $R^1$ or $R^2$, and react the immobilized amine to a mixture of different organoboron compounds (15, where $R^5$ is a variety of different groups) and individual or mixed carbonyl compounds (14) to produce a mixture of bound products (1). Alternatively, the carbonyl compound may be immobilized, and a mixture of organoboron compounds and diverse amines added. Combinatorial libraries may be generated either as individual compounds or as mixtures of compounds.

In another embodiment of the invention an organoboron compound (19) is combined with a preformed iminium derivative (16), aminol (17), or aminal (18), prepared by the combination of an amine (13) and a carbonyl compound (14), or by other methods:

adding Lewis acids, such as compounds containing electron-deficient atoms including boron, lanthanum, silicon, tin, titanium and zinc.

The stereochemistry of the product in these reactions can be controlled by the use of a chiral amine, a chiral carbonyl compound or a chiral organoboron derivative (L. Deloux et al., *Chem. Rev.* (1993) 93:763). The use of chiral amines or similar amino alcohol or amino acid derivatives can give products with a high degree of diastereocontrol (up to 99.5% de). Removal of the chiral group substituent can give the free amino acid with a high enantiomeric excess (up to 99.5% ee).

The types of organoboron compounds that can be used in this manner include compounds 21 that have $R^4$ selected from the group consisting of alkyl, cycloalkyl, aryl,

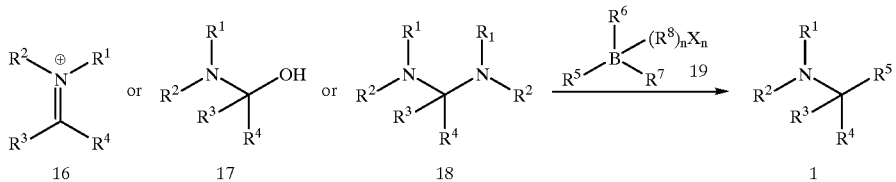

where $R^5$ is selected from the group consisting of alkyl, cycloalkyl, aryl, heteroaryl, alkenyl, alkynyl and allenyl; $R^6$, $R^7$ and $R^8$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms; X is a positive counter ion, and n is 0 or 1. Such reactions can take place directly or upon the addition of a Lewis acid. In the case of fluoroborates (19, $R^6=R^7=R^8=F$) the reaction may be promoted by the addition of a silyl derivative $SiR^9R^{10}R^{11}R^{12}$, where $R^9$ is selected from the groups consisting of: chloro, bromo, iodo, alcoxy, acyloxy, triflate, alkylsulfonate or arylsulfonate, while substituents $R^{10}$, $R^{11}$ and $R^{12}$ are selected from the groups consisting of: alkyl, cycloalkyl, aryl, alkoxy, aryloxy or chloro. A preferred $R^5$ is an alkenyl or aryl group leading to the formation of geometrically and isomerically pure allylamines or benzylamines (2), respectively.

Synthesis of α-amino acid derivatives: This invention can be employed directly for the synthesis of α-amino acids (3) by combining an organoboron compound (21) with an amine (13) and an α-keto acid (20).

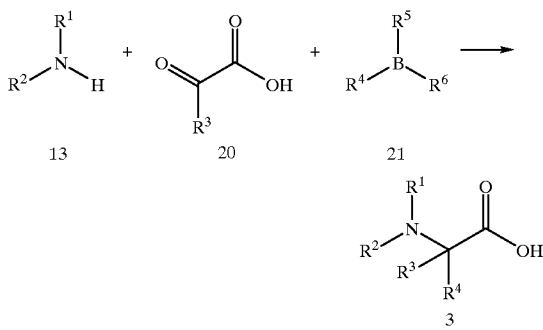

The reaction can proceed directly in a variety of solvents, including water, alcohols, ethers, hydrocarbons, chlorinated hydrocarbons and acetonitrile. It can also be promoted by heteroaryl, alkenyl, alkynyl and allenyl, including substituted and isomerically pure derivatives. The boron substituents $R^5$ and $R^6$ which do not appear in the product 3, are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^5$ and $R^6$ may be connected together to form a bridge of 3 to 7 atoms. Substituents $R^3$ in compound 20 are selected from the group consisting of hydrogen, carboxy, alkyl, cycloalkyl, aryl, hetero aryl, including substituted and isomerically pure derivatives. Substituents $R^1$ and $R^2$ in amine 13 are selected from the groups consisting of: alkyl, cycloalkyl, aryl, heteroaryl, hydroxy, alkoxy, aryloxy, heteroaryloxy, acyl, carboxy, amino, alkylamino, dialkylamino, acylamino, carboxamido, alkylthio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms.

The reactants are combined in approximately equimolar amounts in the solvent, and maintained at a temperature between about 0° C. and the reflux temperature of the solvent, preferably between about 25° C. and about 65° C., until the reaction is complete. The course of the reaction may be followed by any standard method, including thin-layer chromatography, GC and HPLC. In general, the reaction is conducted for about 1 to about 72 hours, preferably about 12 to about 24 hours. Product isolation usually gives fairly pure products without the need for chromatography or distillation.

The products 3 of the invention can be subsequently transformed to produce new derivatives. For example, removing groups $R^1$ and $R^2$ can provide primary amino acids, while joining two or more groups will result in the formation of cyclic or polycyclic derivatives. A number of amine components (13) can be used which include $R^1$ and $R^2$ groups that can be easily removed in subsequent reactions. For example, benzylamine derivatives can be cleaved by hydrogenation, while others, such as the di(p-anisyl) methylamino group or the trityl group, can be removed under acidic conditions which prevent facile racemization.

The multicomponent nature of the process described in this invention allows the direct and rapid generation of combinatorial libraries of the products, by varying the desired substituents. Such libraries can be generated either in solution or in the solid phase, upon attachment of one substituent onto a solid support. For example, one may couple an amine (13) to a substrate through either $R^1$ or $R^2$, and react the immobilized amine with a mixture of different organoboron compounds (21), where $R^4$ is a variety of different groups) and individual or mixed dicarbonyl compounds (20) to produce a mixture of bound products (3). Alternatively, the dicarbonyl compound may be immobilized, and a mixture of organoboron compounds and diverse amines added. Combinatorial libraries may be generated either as individual compounds or as mixtures of compounds.

The present invention is particularly suitable for the synthesis of β,γ-unsaturated-α-amino acids and their derivatives. The required alkenyl boronic acids or boronates (22) can be easily and conveniently prepared from alkynes (A. Suzuki, *Top. Curr. Chem.* (1983) 112:67; E. Negishi et al., *Org. React.* (1985) 33:1; D. S. Matteson, *Chemistry of the Metal Carbon Bond* (1987) 4:307; A. Pelter et al., "Borane Reagents", Academic Press, London, (1988); K. Smith et al., *Comprehensive Organic Synthesis* (1991) 8:703; N. Miyaura et al., *Chem. Rev.* (1995) 95:2457).

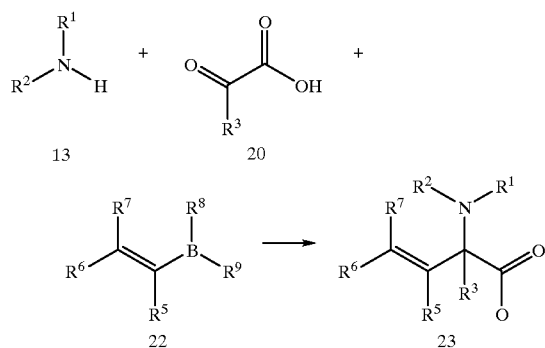

Indeed, reaction of an alkenyl boronic acid or boronate with a mixture of an α-keto acid derivative (such as glyoxylic acid or pyruvic acid) and a primary or secondary amine, gives the corresponding amino acids in high yields. The reaction works in a variety of solvents, including water, ethanol, toluene and dichloromethane. Product isolation is usually straight forward, since the product generally precipitates out and can be isolated by filtration.

Substituents $R^1$ and $R^2$ in the amine component 13 are selected from the group consisting of hydrogen alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected together to form a bridge of 2 to 20 atoms. Substituents $R^3$ in compound 20 are selected from the group consisting of hydrogen, carboxy, alkyl, cycloalkyl, aryl, hetero aryl, including substituted and isomerically pure derivatives. Groups $R^5$, $R^6$ and $R^7$ in compound 22 are selected from the group consisting of alkyl, cycloalkyl, aryl, heteroaryl, alkenyl, alkynyl, allenyl, alkoxy, aryloxy, heteroaryloxy, chloro, bromo, fluoro, iodo, carboxy, amino, alkylamino, dialkylamino, acylamino, carboxamido, thio, alkylthio, arylthio and acylthio,including substituted and isomerically pure derivatives. The boron substituents $R^8$ and $R^9$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives. Groups $R^8$ and $R^9$ may be connected together to form a bridge of 3 to 7 atoms.

The use of other α-dicarbonyl compounds (23) leads to more substituted derivatives (4).

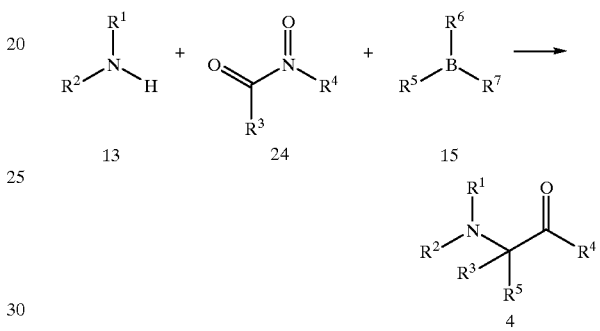

Groups $R^1$ and $R^2$ in the amine component 13 are selected from the group consisting of hydrogen alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected together to form a bridge of 2 to 20 atoms. Substituents $R^3$ and $R^4$ in compound 24 are each independently selected from the group consisting of hydrogen, hydroxy, alkoxy, aryloxy, heteroaryloxy, carboxy, amino, alkylamino, dialkylamino, acylamino, carboxamido, thio, alkylthio, arylthio, acylthio, alkyl, cycloalkyl, aryl, and heteroaryl. The boron substitutent $R^5$ in compound 15 is selected from the group consisting of alkyl, cycloalkyl, aryl, heteroaryl, alkenyl, alkynyl and allenyl. The boron substituents $R^6$ and $R^7$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives. Groups $R^6$ and $R^7$ may be connected together to form a bridge of 3 to 7 atoms.

Synthesis of N-carboxymethyl amino acid derivatives: The use of α-amino acid derivatives (25) as the amine components in this process, leads to N-carboxymethyl amino acid products (5) with a very high degree of diastereocontrol.

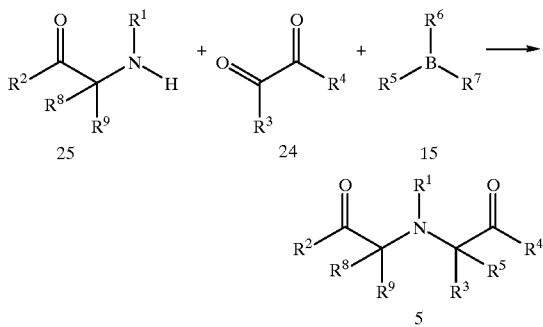

Substituents $R^1$ and $R^2$ in the amino acid component 25 are selected from the group consisting of hydrogen alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected together to form a bridge of 2 to 20 atoms. Groups $R^8$ and $R^9$ are selected from the group consisting of alkyl, cycloalkyl, aryl, hetero aryl, acyl and carboxy,including substituted and isomerically pure derivatives. Groups $R^8$ and $R^9$ may be connected together or with other groups in 25, 24, or 15 to form a bridge of 3 to 7 atoms. Substituents $R^3$ and $R^4$ in compound 24 are each independently selected from the group consisting of hydrogen, hydroxy, alkoxy, aryloxy, heteroaryloxy, carboxy, amino, alkylamino, dialkylamino, acylamino, carboxamido, thio, alkylthio, arylthio, acylthio, alkyl, cycloalkyl, aryl, and heteroaryl. The boron substitutent $R^5$ in 15 is selected from the group consisting of alkyl, cycloalkyl, aryl, heteroaryl, alkenyl, alkynyl and allenyl. The boron substituents $R^6$ and $R^7$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives.

In another preferred empodiment of the invention, the reaction of amino acids or peptides(26) with dicarbonyl compounds (20) and alkenyl boron derivatives (22) gives adducts (27) which can be subsequently hydrogenated to form the ACE inhibitors (9) and (10), as well as other related compounds.

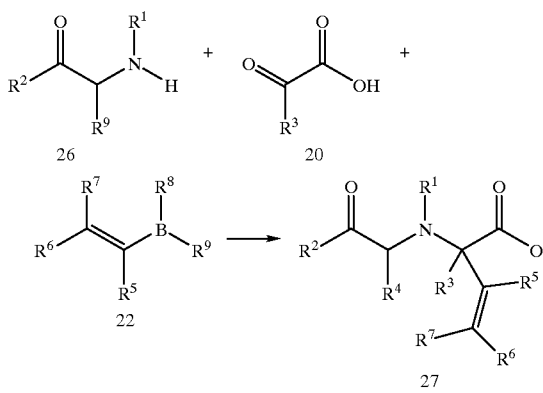

Substituents $R^1$ and $R^2$ in the amino acid component 26 are selected from the group consisting of hydrogen alkyl, cycloalkyl, aryl, heteroaryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected together to form a bridge of 2 to 20 atoms. Group $R^4$ is selected from the groups consisting of: alkyl, cycloalkyl, aryl, hetero aryl, acyl and carboxy,including substituted and isomerically pure derivatives. Groups $R^4$ may be connected together or with other groups in 26, 20, or 22 to form a bridge of 3 to 7 atoms. Group $R^3$ in compound 20 is selected from the group consisting of hydrogen, alkyl, cycloalkyl, aryl, and heteroaryl. Groups $R^5$, $R^6$ and $R^7$ in compound 22 are selected from the groups consisting of: alkyl, cycloalkyl, aryl, heteroaryl, alkenyl, alkynyl, allenyl, alkoxy, aryloxy, heteroaryloxy, chloro, bromo, fluoro, iodo, carboxy, amino, alkylamino, dialkylamino, acylamino, carboxamido, thio, alkylthio, arylthio, acylthio,including substituted and isomerically pure derivatives. The boron substituents $R^8$ and $R^9$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives. Groups $R^8$ and $R^9$ may be connected together to form a bridge of 3 to 7 atoms.

Synthesis of 1,2-diamines and 1,2-amino alcohols: In another empodiment of the invention an amine (13) and an organoboron compound are reacted with carbonyl derivatives of the general formula 28 to give products 29.

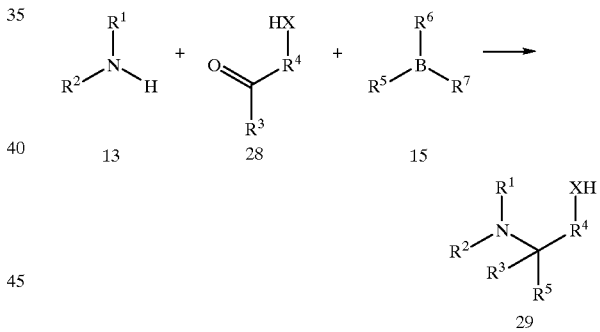

Groups $R^1$ and $R^2$ in the amine component 13 are selected from the groups consisting of: hydrogen alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms. Groups $R^3$ in compound 28 are selected from the group consisting of hydrogen, alkyl, cycloalkyl, aryl, and heteroaryl. Groups $R^4$ in compound 28 have at least one carbon atom and are attached to a group XH, where X is selected from a group consisting of —O—, —$R_a$—, —S—, and $R_a$ is independently selected from the group consisting of hydrogen, alkyl, aryl, heteroaryl, acyl, hydroxy, alkoxy, aryloxy, heteroaryloxy, amino, alkylamino, dialkylamino, and acylamino. The boron substitutent $R^5$ in compound 15 is selected from the group consisting of alkyl, cycloalkyl, aryl, heteroaryl, alkenyl, alkynyl and allenyl. The boron substituents $R^6$ and $R^7$ which do not appear in the products, are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^6$ and $R^7$ may be connected together to form a bridge of 3 to 7 atoms.

In one empodiment of the invention an amine (13) and an organoborn compound are reacted with α-amino carbonyl derivatives (30) to give 1,2-diamines (6).

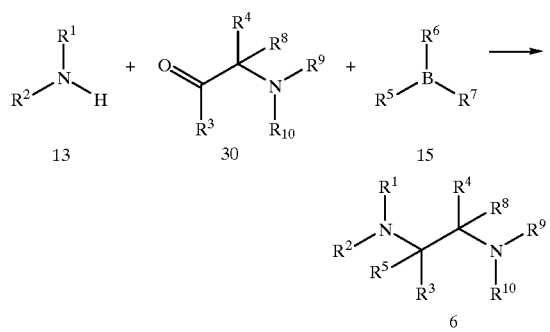

Groups $R^1$ and $R^2$ in the amine component 13 are selected from the groups consisting of: hydrogen alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms. Groups $R^3$, $R^4$ and $R^8$ in compound 30 are selected from the group consisting of hydrogen, alkyl, cycloalkyl, aryl, and heteroaryl. Groups $R^9$ and $R^{10}$ in compound 30 are selected from the group consisting of alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^9$ and $R^{10}$ may be connected with other groups in compounds 13, 30 or 15 to form a bridge of 2 to 20 atoms. The boron substitutent $R^5$ in compound 15 is selected from the group consisting of alkyl, cycloalkyl, aryl, heteroaryl, alkenyl, alkynyl and allenyl. The boron substituents $R^6$ and $R^7$ which do not appear in the products, are selected from the group consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives. Groups $R^6$ and $R^7$ may be connected together to form a bridge of 3 to 7 atoms.

The products 6 of the invention can be subsequently transformed to produce new derivatives. For example, removing groups $R^1$ and $R^2$ can provide primary amines, while joining two or more groups will result in the formation of cyclic or polycyclic derivatives. A number of amine components (13) can be used which include $R^1$ and $R^2$ groups that can be easily removed in subsequent reactions. For example, benzylamine derivatives can be cleaved by hydrogenation, while others, such as the di(p-anisyl) methylamino group or the trityl group, can be removed under acidic conditions which prevent facile racemization.

In another empodiment of the invention an amine (13) and an organoboron compound are reacted with an α-hydroxy carbonyl derivative (31) to give 1,2-amino alcohols (7). Compounds 31 can also exist in a hemiacetal form, and can include carbohydrate derivatives. The use of chiral derivatives 31 forms products 7 with a very high degree of diastereocontrol (up to 99.5% de).

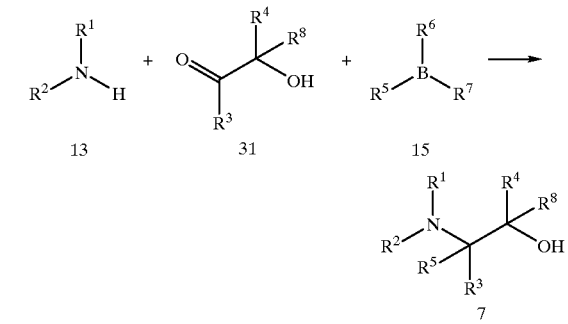

Groups $R^1$ and $R^2$ in the amine component 13 are selected from the group consisting of hydrogen alkyl, cycloalkyl, aryl, heteroaryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected with other groups in compounds 13, 31 or 15 to form a bridge of 2 to 20 atoms. Groups $R^3$, $R^4$ and $R^8$ in compound 31 are selected from the group consisting of hydrogen, alkyl, cycloalkyl, aryl, and heteroaryl. The boron substitutent $R^5$ in compound 15 is selected from the group consisting of alkyl, cycloalkyl, aryl, heteroaryl, alkenyl, alkynyl and allenyl. The boron substituents $R^6$ and $R^7$ which do not appear in the products, are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^6$ and $R^7$ may be connected together to form a bridge of 3 to 7 atoms.

The products 7 of the invention can be subsequently transformed to produce new derivatives. For example, removing groups $R^1$ and $R^2$ can provide primary amines, while joining two or more groups will result in the formation of cyclic or polycyclic derivatives. A number of amine components (13) can be used which include $R^1$ and $R^2$ groups that can be easily removed in subsequent reactions. For example, benzylamine derivatives can be cleaved by hydrogenation, while others, such as the di(p-anisyl) methylamino group or the trityl group, can be removed under acidic conditions which prevent facile racemization. Also, the use of groups $R^5$ in the organoboron component, such as alkenyl or activated aryl or heteroaryl, followed by oxidative cleavage gives new products where the $R^5$ is a carbonyl group (aldehyde, ketone or carboxylic acid). One such example are compounds of the general formula 8, which include 2-amino sugar derivatives that exist in a hemiacetal form. Alternatively, the use of carbonyl components 31 having a group $R^4$ or $R^8$ consisting of a carbon atom attached to a hydroxyl group, as with many carbohydrate derivatives, followed by oxidative diol cleavage can produce new variations of compounds of the general formula 2.

Advantages and Improvements Over Existing Technology

Although there are many known methods for the synthesis of amines and amino acids, due to the vital importance of these compounds and the many shortcomings of existing methods, any conceptually new and practical method in this are is of special significance. The present method offers a number of advantages over existing methods, including:

1. This new method for amino acid synthesis is exceptionally environmentally friendly and practical. The reactions can be done in water or aqueous solvents at ambient temperature without using any toxic, hazardous or corrosive materials, such as cyanides, isonitriles, strong acids, strong bases, organotin, organocopper or other highly reactive organometallic compounds. Also, the reaction does not require an inert atmosphere, and can be done in the air.

2. Unlike other methods which involve multistep manipulations of one amino acid into another, the method of the invention offers direct asymmetric construction of the amino acid structural unit from simple building blocks (amine, α-ketoacid and boronic acid or boronate).

3. Existing procedures for preparing β,γ-unsaturated-α-amino acids suffer either from low efficiency and low stereoselectivity or from the need to use highly toxic reagents. The method of the invention offers a direct, efficient and highly versatile synthetic route to this important class of compounds.

4. The present method involves a smaller number of synthetic steps than most existing methods. All starting materials used in this type of reaction are either commercially available or can be readily prepared from commercially available reagents by a one-step procedure.

5. Product isolation and purification in the present method is much easier than with existing methods. In most cases, the product precipitates during the course of the reaction, and can be isolated by a simple filtration and washing, without the need for laborious purification procedures, such as extraction, distillation or chromatography.

The use of organoboron compounds, particularly boronic acids and boronates, as nucleophilic components for amino acid and amine synthesis is a new concept which offers a number of distinct features, including the following:

1. Organoboronic acids are often crystalline, easy to prepare and easy to handle compounds that are stable in air and water. They are also non toxic and non hazardous. Although the synthesis and reactivity of these molecules has been studied extensively, the present method is the first successful example of their utilization in the synthesis of amines and amino acids.

2. Although the present method may appear similar to the Strecker and Ugi methods for amino acid synthesis, it is conceptually different from them. The nucleophilic component in the Strecker and Ugi methods is an equivalent of the carboxylic acid moiety (cyanide or isonitrile) while in the present method the nucleophilic component is a boron derivative of the amino acid side chain. In this manner, the amine component is combined with a more standard carbonyl component (e.g., glyoxylic acid) and the only real variable in each case is the amino acid side chain. The fact that the organoboron compounds used in the present method do not react directly with the carbonyl component gives them a unique advantage and makes the overall reaction more selective.

3. The present method is highly versatile, allowing a high degree of structural variation in all of the reacting components. The process is also a multi-component reaction, allowing the one-pot construction of amino acid derivatives from several readily available building blocks. For these reasons, this method is easily applicable to the solid or liquid phase combinatorial synthesis of peptides and peptidomimetics.

4. The stereochemical control of the reaction can be accomplished not only with the use of chiral amine and carbonyl components but also with chiral organoboron derivatives. An advantage of boron-based auxiliaries is that they can be easily introduced and can be efficiently recycled after the reaction, thus making this method especially attractive for large scale applications.

5. Due to the facile synthesis of alkenyl and aryl boron derivatives, which proceed with complete control of geometry or positional isomerism, the present method is uniquely capable of furnishing isomerically pure products of this type.

6. Of special significance is the ability to directly use free amino acids in this reaction. This leads to N-carboxymethyl amino acid derivatives, which are peptidomimetic compounds with important pharmaceutical properties.

EXAMPLES

The following examples are put forth so as to provide those of ordinary skill in the art with a complete disclosure and description of how to perform the processes of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Tables I–VII, summarize a number of reactions from several types of amines, carbonyls and organoboron compounds that have been utilized in this process. Subsequently, representative experimental procedures and structural data of the obtained products are given.

TABLE I

| Conditions | | Product | Yield |
|---|---|---|---|
| 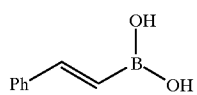 | CHOCOOH·H₂O EtOH, 25° C. | 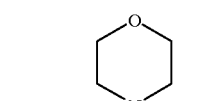 | 91% |

TABLE I-continued
| Conditions | Product | Yield |
|---|---|---|
| 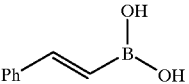 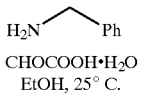 CHOCOOH·H₂O EtOH, 25° C. | 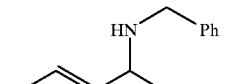 | 87% |
| 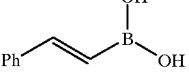 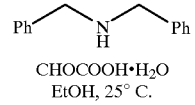 CHOCOOH·H₂O EtOH, 25° C. | 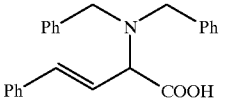 | 90% |
| 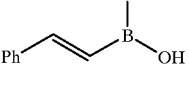 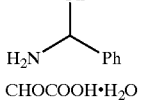 CHOCOOH·H₂O PhMe, 25° C. | 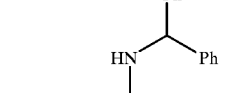 | 95% |
| 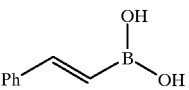 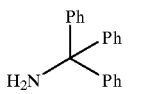 CHOCOOH·H₂O EtOH, 25° C. | 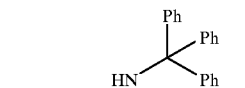 | 54% |
| 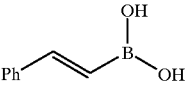 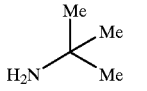 CHOCOOH·H₂O PhMe, 25° C. | 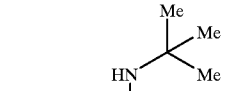 | 68% |
| 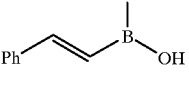  CHOCOOH·H₂O CH₂Cl₂, 25° C. | 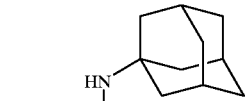 | 96% |
TABLE II
| Conditions | Product | Yield |
|---|---|---|
| 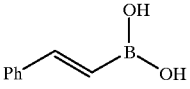 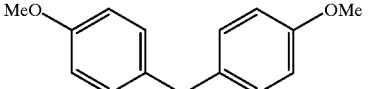 CHOCOOH·H₂O PhMe, 25° C. | 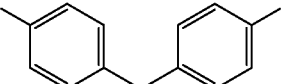 | 89 |

TABLE II-continued

| Conditions | | Product | Yield |
|---|---|---|---|
| 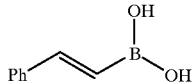 Ph-CH=CH-B(OH)₂ | 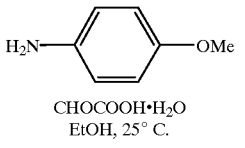 H₂N-C₆H₄-OMe<br>CHOCOOH·H₂O<br>EtOH, 25° C. | 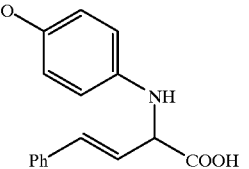 MeO-C₆H₄-NH-CH(COOH)-CH=CH-Ph | 94% |
| 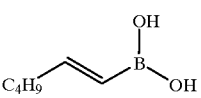 C₄H₉-CH=CH-B(OH)₂ | 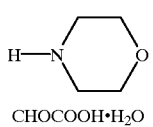 morpholine H-N(CH₂CH₂)₂O<br>CHOCOOH·H₂O<br>EtOH, 45° C. | 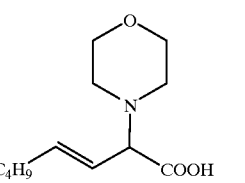 morpholino-CH(COOH)-CH=CH-C₄H₉ | 78% |
| 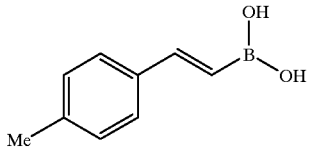 4-Me-C₆H₄-CH=CH-B(OH)₂ | 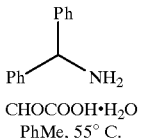 Ph₂CH-NH₂<br>CHOCOOH·H₂O<br>PhMe, 55° C. | 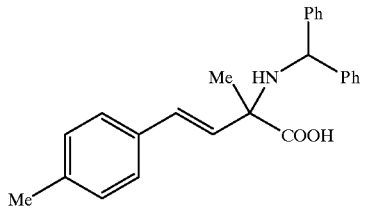 4-Me-C₆H₄-CH=CH-C(Me)(NHCHPh₂)-COOH | 76% |
| 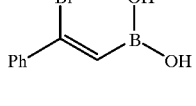 Ph-C(Br)=CH-B(OH)₂ | 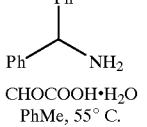 Ph₂CH-NH₂<br>CHOCOOH·H₂O<br>PhMe, 55° C. | 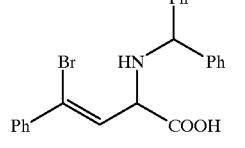 Ph-C(Br)=CH-CH(NHCHPh₂)-COOH | 87% |
| 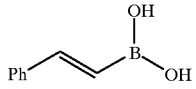 Ph-CH=CH-B(OH)₂ | 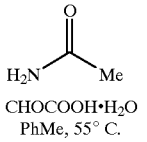 H₂N-C(O)-Me<br>CHOCOOH·H₂O<br>PhMe, 55° C. | 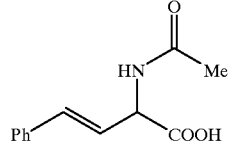 Ph-CH=CH-CH(NHC(O)Me)-COOH | 52% |

TABLE III

| Chiral amine | Conditions | Product | Yield % (% de) |
|---|---|---|---|
| 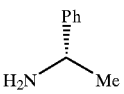 (R)-PhCH(Me)NH₂ | 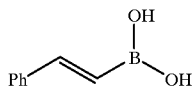 Ph-CH=CH-B(OH)₂<br>CHOCOOH·H₂O<br>CH₂Cl₂, 25° C. | 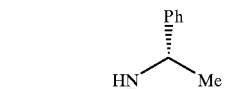 Ph-CH=CH-CH(COOH)-NH-CH(Me)Ph | 88% (66% de) |

TABLE III-continued

| Chiral amine | Conditions | Product | Yield % (% de) |
|---|---|---|---|
| (S)-α-methylbenzylamine (H₂N-CH(Ph)Me) | vinyl boronate with (R,R)-diethyl tartrate ester; CHOCOOH·H₂O, PhMe, 25° C. | (E)-PhCH=CH-CH(NHCH(Ph)Me)-COOH | 88% (89% de) |
| (S)-α-methylbenzylamine | (E)-PhCH=CH-B(OH)₂; CHOCOOH·H₂O, CH₂Cl₂, 25° C. | β-amino-γ-hydroxy product with PH group | 91% (83% de) |
| (S)-α-methylbenzylamine | (E)-PhCH=CH-B(OH)₂; CHOCOOH·H₂O, CH₂Cl₂, 25° C. | (E)-PhCH=CH-CH(NHCH(Ph)Me)-COOH with CH₂OH | 78% (99% de) |
| (S,S)-diphenyl aminoethanol | boronate; CHOCOOH·H₂O, CH₂Cl₂, 25° C. | (E)-PhCH=CH-CH(NHCH(Ph)CH₂OH)-COOH | 78% (99% de) |
| | ↓ H₂, Pd/C<br>MeOH, HCl, Et₂O | Ph-CH₂-CH₂-CH(NH₃⁺Cl⁻)-COOH | 76% (99% ee) |

TABLE IV

| Amino acid | Conditions | Product | Yield % (% de) |
|---|---|---|---|
| H₂N-CH(Me)-COOH (alanine) | (E)-PhCH=CH-B(OH)₂; CHOCOOH·H₂O, MeOH, 25° C. | (E)-PhCH=CH-CH(NHCH(Me)COOH)-COOH | 79% (99% de) |

TABLE IV-continued
| Amino acid | Conditions | Product | Yield % (% de) |
|---|---|---|---|
| 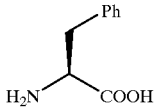 | 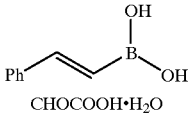<br>CHOCOOH·H₂O<br>MeOH, 25° C. | 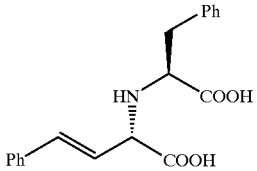 | 89% (99% de) |
| 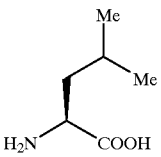 | 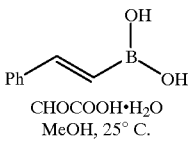<br>CHOCOOH·H₂O<br>MeOH, 25° C. | 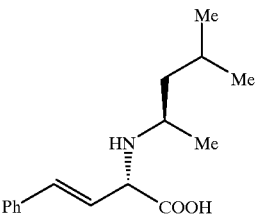 | 85% (94% de) |
| 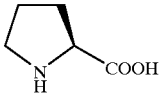 | 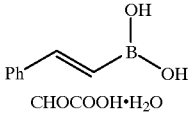<br>CHOCOOH·H₂O<br>MeOH, 25° C. | 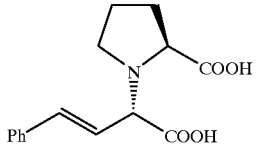 | 83% (24% de) |
| 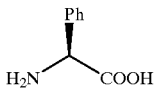 | 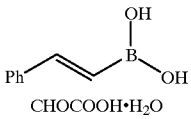<br>CHOCOOH·H₂O<br>MeOH, 25° C. | 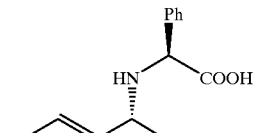 | 47% (>99% de) |
| 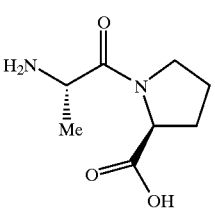 | 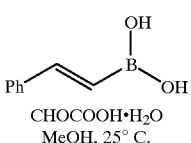<br>CHOCOOH·H₂O<br>MeOH, 25° C. | 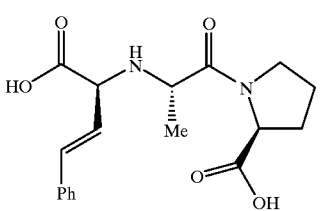<br>↓ H₂, Pd/C<br>MeOH<br>Enalaprilat | 95% (>99% de)<br><br><br><br>95% (>99% de) |

TABLE V

| Conditions | Product | Yield |
|---|---|---|

Row 1: 4-X-phenylboronic acid + H₂N-CHPh₂ + CHOCOOH·H₂O in CH₂Cl₂ or PhMe → 2-(4-X-phenyl)-2-(benzhydrylamino)acetic acid

- X = H — 84%
- X = F — 50%
- X = Br — 71%
- X = OMe — 85%
- X = CH=CH$_2$ — 90%

Row 2: Thiophen-3-yl boronic acid + H₂N-CHPh₂ + CHOCOOH·H₂O in CH₂Cl₂, 25° C. → 2-(thiophen-3-yl)-2-(benzhydrylamino)acetic acid — 92%

Row 3: PS-PEG-CH₂-NH-C(O)-CH₂-O-C₆H₄-CH(NH₂)-C₆H₃(OMe)₂ (Polystyrene Polyethyleneglycol resin-bound amine) + 2-thienylboronic acid + CHOCOOH·H₂O, 1:1 PhMe/CH₂Cl₂, 25° C., then TFA, CH₂Cl₂, then HCl, H₂O → 2-(thiophen-2-yl)glycine hydrochloride — 80%

TABLE VI

| Conditions | Product | Yield % (% de) |
|---|---|---|
| Bu-CH=CH-B(OH)₂ + morpholine (NH); HO-dioxane-OH; EtOH, 25° C. | Bu-CH=CH-CH(N-morpholine)-CH₂OH | 75% |
| Ph-CH=CH-B(OH)₂ + H₂N-CH(Ph)-COOH; HO-dioxane-OH; MeOH, 25° C. | Ph-CH=CH-CH(NH-CH(Ph)COOH)-CH₂OH | 54% (>99% de) |
| Ph-CH=CH-B(OH)₂ + Ph₂CH-NH₂; glyceraldehyde (OHC-CH(OH)-CH₂OH); EtOH, 25° C. | Ph-CH=CH-CH(NH-CHPh₂)-CH(OH)-CH₂OH | 88% (>99% de) |
| 4-MeO-C₆H₄-B(OH)₂ + PhCH₂-N(Me)H; glyceraldehyde; EtOH, 25° C. | 4-MeO-C₆H₄-CH(N(Me)CH₂Ph)-CH(OH)-CH₂OH | 72% (>99% de) |
| 2-thienyl-B(OH)₂ + (PhCH₂)₂NH | 2-thienyl-C(N(CH₂Ph)₂)(CH₂OH)₂ | 78% |

TABLE VI-continued
| Conditions | Product | Yield % (% de) |
|---|---|---|
| 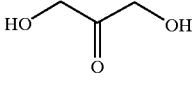 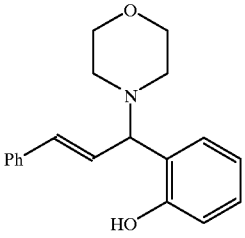 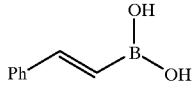  EtOH, 25° C. | 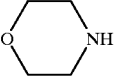 | 88% |
TABLE VII
| Conditions | Product | Yield % (% de) |
|---|---|---|
| 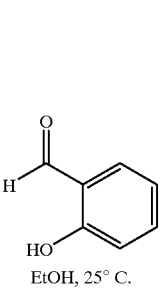 (D)-Ribose 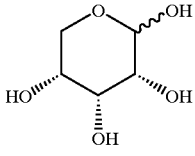 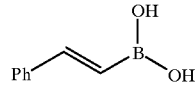  EtOH, 25° C. | 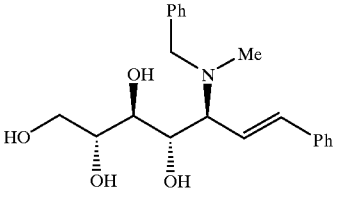 | 74% (>99% de) |
| 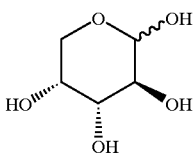 (D)-Arabinose 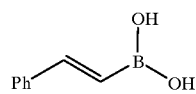 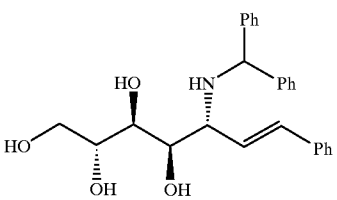 | | 77% (>99% de) |

TABLE VII-continued

| Conditions | Product | Yield % (% de) |
|---|---|---|

(D)-Xylose, EtOH, 25° C., with H₂N-CH(CH₂Ph)-COOH and furan-2-boronic acid → product: 67% (>99% de)

(D)-Arabinose, EtOH, 25° C., with (E)-PhCH=CH-B(OH)₂ and bis(4-methoxyphenyl)methylamine → intermediate → 1. AcOH, H₂O; 2. (Boc)₂O → NHBoc alkene → O₃, then Me₂S → pyranose-NHBoc product, 39% overall

Example 1

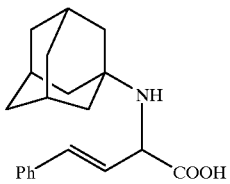

Preparation of (E)-2-(N-adamantyl)-amino-4-phenyl-3-butenoic acid.

To a stirred solution of glyoxylic acid monohydrate (88 mg, 0.957 mmol) in dichloromethane (7 mL) was added 1-adamantanamine (144 mg, 0.957 mmol) in one portion. After 5 min, (E)-2-phenylethenyl boronic acid (141 mg, 0.957 mmol) was added and the reaction mixture was stirred vigorously at room temperature for 12 hours. The precipitate was isolated by filtration, washed with dichloromethane (15 mL) and cold acetone (10 mL) and dried under vacuum to give (E)-2-(N-adamantyl)-amino-4-phenyl-3-butenoic acid (284 mg, 96% yield). $^1$H-NMR (360 MHz, DCl/D$_2$O) δ 6.8–7.2 (m, 5H), 6.68 (d, J=15.7 Hz, 1H), 5.96 (dd, J=15.7 Hz, 9.2 Hz, 1H), 4.63 (d, J=9.2 Hz, 1H), 1.2–1.8 (m, 15H). $^{13}$C-NMR (90 MHz, D$_2$O-DCl) δ 170.9, 140.2, 135.5, 130.3, 129.8, 128.0, 119.1, 62.0, 56.9, 40.8, 39.4, 35.5, 29.8. Anal. Calcd for C$_{21}$H$_{29}$NO$_2$: C, 77.03; H, 8.93; N, 4.28. Found: C, 77.01; H, 8.83; N, 4.34.

Example 2

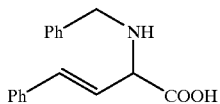

Preparation of (E)-2-(N-benzyl)-amino-4-phenyl-3-butenoic acid.

To a stirred solution of benzylamine (120 mg, 1.120 mmol) in ethanol (5 mL) was added dropwise the solution of glyoxylic acid monohydrate (103 mg, 1.120 mmol) in ethanol (3 mL). After 5 min, (E)-2-phenylethenyl boronic acid (165 mg, 1.115 mmol) was added in one portion and the reaction mixture was stirred vigorously at room temperature for 12 hours. The precipitate was isolated by filtration, washed with dichloromethane (15 mL), cold acetone (10 mL) and dried under vacuum to give (E)-2-(N-benzyl)-amino-4-phenyl-3-butenoic acid (259 mg, 87% yield). $^1$H-NMR (360 MHz, d$_6$-DMSO ) δ 7.2–7.5 (m, 10H), 6.68 (d, J=15.6 Hz, 1H), 6.22 (dd, J=15.6 Hz, 7.9 Hz, 1H), 3.90 (s, 2H), 3.82 (d, J=7.9 Hz, 1H).

$^{13}$C-NMR (90 MHz, d$_6$-DMSO) δ 171.23, 136.31, 133.22, 129.04, 128.68, 128.47, 128.37, 128.18, 127.97, 127.74, 126.90, 63.49, 49.21.

Anal. Calcd for $C_{17}H_{17}NO_2$: C, 76.38; H, 6.41; N, 5.24. Found: C, 76.31; H, 6.44; N, 5.23.

Example 3

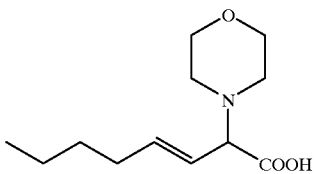

Preparation of (E)-2-morpholino-3-octenoic acid.

To a stirred solution of glyoxylic acid monohydrate (80 mg, 0.87 mmol) in ethanol (6 mL) was added morpholine (76 mg, 0.87 mmol) in one portion. After 5 min (E)-1-hexenyl boronic acid (121 mg, 0.82 mmol) was added. The reaction mixture was heated at 50° C. for 36 hours, after which time precipitate was isolated by filtration, washed with cold ethanol (10 mL) and dried under vacuum to give (E)-2-morpholino-3-octenoic acid (177 mg, 78% yield). $^1$H-NMR (360 MHz, d$_6$-DMSO) δ 5.65 (dt, J=16.1 Hz, 7.0 Hz, 1H), 5.28 (dd, J=16.1 Hz, 9.1 Hz, 1H), 4.81 (d, J=9.1 Hz, 1H), 2.50 (m, 2H), 1.1 (m, 4H), 0.7 (t, J=7.1 Hz, 3H). $^{13}$C-NMR (90 MHz, d$_6$-DMSO) δ 171.1, 136.7, 127.4, 68.8, 62.5, 56.7, 31.7, 30.2, 22.1, 13.9. HRMS-CI (M$^+$+1) Calcd for $C_{12}H_{21}NO_3$: 228.1521, Found: 228.1513.

Example 4

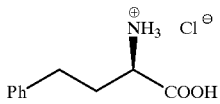

Preparation of D-homophenylalanine.

To a stirred solution of glyoxylic acid monohydrate (291 mg, 3.163 mmol) in dichloromethane (14 mL) was added (S)-(−)-2-phenylglycinol (434 mg, 3.163 mmol) in one portion. After 5 min (E)-2-phenylethenyl boronic acid (469 mg, 3.169 mmol) was added. and the reaction mixture was stirred vigorously at room temperature for 12 hours. The precipitate was isolated by filtration, washed with cold dichloromethane (15 mL) and acetone (10 mL) and dried under vacuum to give the expected adduct (733 mg, 78% yield, >99% de). $^1$H-NMR (360 MHz, d$_6$-DMSO) δ 7.2–7.5 (m, 10H), 6.54 (d, J=15.2 Hz, 1H), 6.20 (dd, J=15.2 Hz, 7.3 Hz, 1H), 3.84 (m, 1H), 3.64 (d, J=7.3 Hz, 1H), 3.45 (d, J=7.1 Hz, 2H).

$^{13}$-NMR (90 MHz, d$_6$-DMSO) δ 172.83, 139.79, 136.23, 131.07, 128.62, 128.34, 127.68, 127.51, 126.95, 126.38, 126.25, 65.97, 63.02, 60.96. HRMS-CI(M$^+$+1) calcd 298.1365, obsd 298.1449. Anal. Calcd for $C_{18}H_{19}NO_3$: C, 72.71; H, 6.44; N, 4.71. Found: C, 72.27; H, 6.41 N, 4.69.

To a suspension of the above compound (150 mg, 0.505 mmol) and Pearlman's catalyst (50 mg) in methanol (10 mL) was added a hydrochloric acid solution in diethyl ether (3 mL) and the reaction mixture was vigorously stirred under an atmosphere of hydrogen gas for 48 hours. The catalyst was removed by filtration and the solution was evaporated to dryness. The resulting residue was suspended in dichloromethane (10 mL) and the white precipitate was isolated by filtration, washed with dichloromethane (10 mL) and dried under vacuum to give D-homophenylalanine (69 mg, 76% yield). Using Mosher's acid chloride the product was determined to have 98% ee. All properties of the compound obtained were consistent with a commercially available authentic sample.

$^1$H-NMR (360 MHz, d$_6$-DMSO) δ 7.2–7.5 (m, 5H), 3.83 (t, J=6.1 Hz, 1H), 2.70 (m, 2H), 2.08 (m, 2H). $^{13}$C-NMR (90 MHz, d$_6$-DMSO) δ 170.8, 140.5, 128.5, 128.3, 126.2, 51.6, 31.9, 30.4. HRMS-CI (M$^+$+1) calcd 180.0946, obsd 180.1029. $[α]^{21}_D$=−46.0° (C=1, 3N HCl).

Example 5

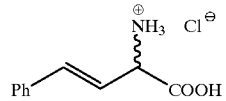

Preparation of (E)-2-amino-4-phenyl-3-butenoic acid.

To a stirred solution of glyoxylic acid (110 mg, 1.2 mmol) in toluene (12 mL) was added di-(p-anisyl)-methylamine (291 mg, 1.2 mmol) in one portion. After 1 min, 2-phenylethenyl boronic acid (177 mg, 1.2 mmol) was added and the reaction mixture was stirred vigorously for 12 hours. The precipitated product was isolated by filtration, washed with dichloromethane (15 mL), toluene (10 mL) and dried under vacuum to give the expected product (430 mg, 89% yield). $^1$H-NMR (360 MHz, CD$_3$OH) d 6.8–7.5 (m, 13H), 6.60 (d, J=15.5 Hz, 1H), 6.25 (dd, J=15.5 Hz, 9.5 Hz, 1H), 5.49 (s, 1H), 4.00 (d, J=9.5 Hz, 1H), 3.75 (s, 6H), 2.3 (s, 1H).

$^{13}$C-NMR (360 MHz, CD$_3$OH) d 171.55, 161.60, 161.52, 138.91, 137.06, 130.56, 130.39, 129.92, 129.74, 129.64, 129.51, 129.20, 128.84, 127.89, 126.30, 121.54, 115.66, 115.52, 65.06, 65.02, 55.81.

The above product (210 mg, 0.52 mmol) was dissolved in 50% acetic acid (10 mL) and heated under reflux at 80° C. for 20 min. After cooling to ambient temperature, the reaction mixture was further acidified with 3N HCl (3 mL) and extracted with diethyl ether (2×10 mL). Evaporation of water resulted in a solid, which was transferred to the glass filter with the help of a little amount of dichloromethane and dried to give the hydrochloride salt of (E)-2-amino-4-phenyl-3-butenoic acid (75 mg, 81% yield). $^1$H-NMR (360

MHz, DCl/D$_2$O) δ 6.6–6.8 (m, 5H), 6.21 (d, J=15.9 Hz, 1H), 5.60 (dd, J=15.9 Hz, 9.0 Hz, 1H), 4.12 (d, J=9.0 Hz, 1H). $^{13}$C-NMR (90 MHz, D$_2$O-DCl) δ 170.2, 138.6, 134.8, 129.2, 128.9, 127.0, 118.0, 54.7.

Example 6

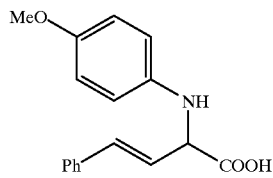

Preparation of (E)-2-(N-p-methoxyphenyl)-amino-4-phenyl-3-butenoic acid.

To a stirred solution of glyoxylic acid monohydrate (88 mg, 0.957 mmol) in dichloromethane (7 mL) was added p-methoxyaniline (118 mg, 0.958 mmol) in one portion. After 5 min, (E)-2-phenylethenyl boronic acid (141 mg, 0.957 mmol) was added and the reaction mixture was stirred vigorously at room temperature for 12 hours. The precipitate was isolated by filtration, washed with dichloromethane (15 mL) and cold acetone (10 mL), and dried under vacuum to give the amino acid product (284 mg, 96% yield).

$^1$H-NMR (360 MHz, d$_6$-DMSO) δ 6.5–7.5 (m, 10H), 6.35 (dd, J=15.5 Hz, 5.9 Hz, 1H), 4.62 (d, J=5.9 Hz, 1H), 3.66 (s, 3H).

$^{13}$C-NMR (90 MHz, d$_6$-DMSO) δ 173.3, 151.3, 141.3, 136.1, 131.6, 128.7, 127.8, 126.4, 126.3, 114.4, 114.0, 58.9, 55.8.

Anal. Calcd for C$_{17}$H$_{17}$NO$_3$: C, 72.07; H, 6.05; N, 4.94. Found: C, 72.10; H, 6.02; N, 4.85.

Example 7

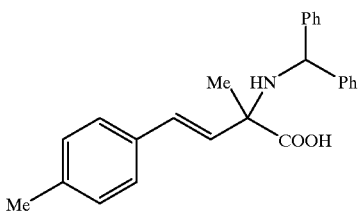

This compound was prepared as in example 6, but substituting aminodiphenylmethane for p-methoxyaniline and 2-(4-methylphenyl) ethenyl boronic acid for 2-phenylethenyl boronic acid. $^1$H-NMR (360 MHz, d$_6$-DMSO) δ 7.0–7.5 (m, 14H), 6.48 (d, J=16.0 Hz, 1H), 6.20 (d, J=16.0 Hz, 1H), 4.93 (s, 1H), 2.26 (s, 3H), 1.22 (s, 3H).

$^{13}$C-NMR (90 MHz, d$_6$-DMSO) δ 175.7, 145.7, 145.6, 136.9, 133.63, 131.8, 129.14, 128.8, 128.3, 127.1, 127.0, 126.6, 126.3, 63.9, 62.2, 22.7, 20.8.

Anal. Calcd for C$_{25}$H$_{25}$NO$_2$: C, 80.83; H, 6.78; N, 3.77. Found: C, 81.02; H, 6.72; N, 3.74.

Example 8

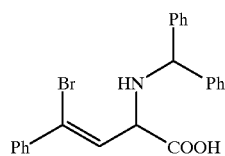

This compound was prepared as in example 7, but substituting 2-bromo-2-phenyl boronic acid for 2-(4-methylphenyl) ethenyl boronic acid. $^1$H-NMR (360 MHz, d$_6$-DMSO) δ 7.1–7.6 (m, 15H), 6.48 (d, J=8.7 Hz, 1H), 4.95 (s, 1H), 4.15 (d, J=8.7 Hz, 1H).

$^{13}$C-NMR (90 MHz, d$_6$-DMSO) δ 172.2, 143.4, 138.4, 129.5, 129.1, 128.9, 128.4, 128.3, 127.3, 127.2, 126.9, 63.9, 61.5.

Anal. Calcd for C$_{23}$H$_{20}$BrNO$_2$: C, 65.41; H, 4.77; N, 3.32. Found: C, 65.66; H, 4.97; N, 3.22.

Example 9

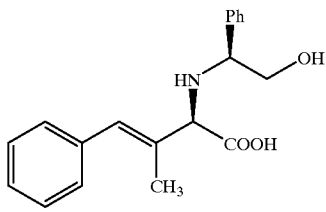

The reaction was run as in example 6, for 48 hours in dichloromethane in 43% isolated yield, >99% de.

$^1$H NMR (360 MHz, DMSO-d$_6$) δ 7.00–7.48 (m, 10H), 6.25 (s, 1H), 3.79 (m, 1H), 3.59 (s, 1H), 3.45 (m, 2H), 1.82 (s, 3H).

$^{13}$C NMR (90 MHz, DMSO-d$_6$) δ 173.2, 140.5, 137.2, 135.7, 129.0, 128.6, 128.5, 128.1, 127.9, 127.8, 126.9, 67.5, 66.2, 64.2, 15.4.

Example 10

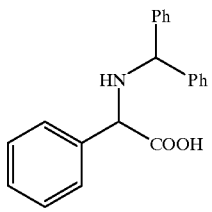

Preparation of (±)-N-(diphenylmethyl)-α-phenylalycine.

To a stirred solution of glyoxylic acid monohydrate (92 mg, 1 mmol) in dichloromethane (7 mL) was added aminodiphenylmethane (183 mg, 1 mmol), followed by phenylboronic acid (122 mg, 1 mmol). After the flask was purged with argon and sealed, the reaction mixture was stirred vigorously at room temperature for 48 h. The resulting precipitate was isolated by filtration, washed with dichloromethane (10 mL) and purified by ion-exchange chromatography (Dowex 50W-X8) to give pure (±)-N-(diphenylmethyl)-α-phenylglycine (266 mg, 84% yield).

$^1$H-NMR (360 MHz, DMSO-d$_6$) δ 7.0–7.8 (m, 15H), 4.78 (s, 1H), 4.17 (s, 1H); $^{13}$C-NMR (90 MHz, DMSO-d$_6$) δ

172.8, 142.4, 133.6, 129.6, 128.1, 127.5, 127.1, 126.9, 126.7, 63.6, 62.2.

Anal. calcd for $C_{21}H_{19}NO_2$: C, 79.47; H, 6.03; N, 4.41; found: C, 79.48; H, 6.17; N, 4.32.

Example 11

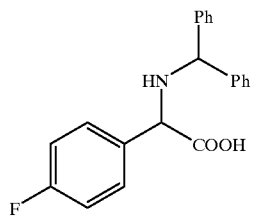

Preparation of (±)-N-(diphenylmethyl)-α-(4-fluorophenyl)glycine.

Prepared similarly to (±)-N-(diphenylmethyl)-α-phenylglycine in 50% yield. $^1$H-NMR (250 MHz, DMSO-$d_6$) δ 7.15–7.92 (m, 14H), 4.72 (s, 1H), 4.12 (s, 1H); $^{13}$C-NMR (63 MHz, DMSO-$d_6$) δ 173.2, 163.3, 159.7, 143.3, 143.2, 134.7, 129.3, 129.2, 128.3, 128.2, 127.0, 115.2, 114.9, 63.9, 61.8; $^{19}$F-NMR (339 MHz, DMSO-$d_6$) δ −114.6 (br).

Example 12

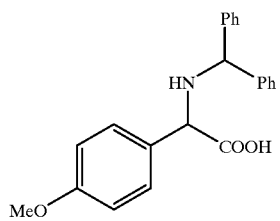

Preparation of (±)-N-(diphenylmethyl)-α-(4-methoxyphenyl)glycine.

Prepared similarly to (±)-N-(diphenylmethyl)-α-phenylglycine in toluene (85% yield). $^1$H-NMR (250 MHz, acetone-$d_6$) δ 7.16–7.45 (m, 12H), 6.89–6.92 (m, 2H), 4.80 (s, 1H), 4.20 (s, 1H) 3.78 (s, 3H); $^{13}$C-NMR (63 MHz, acetone-$d_6$) δ 174.2, 160.3, 144.6, 131.4, 129.7, 129.5, 129.3, 129.2, 128.2, 127.9, 127.8, 114.7, 114.6, 65.1, 62.8, 55.5.

Example 13

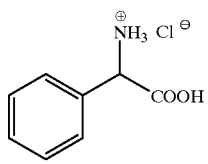

Preparation of (±)-α-phenylglycine hydrochloride.

To a stirred solution of glyoxylic acid monohydrate (184 mg, 2 mmol) in toluene (10 mL) was added di(p-anisyl)methyl amine (486 mg, 2 mmol), followed by phenylboronic acid (244 mg, 2 mmol). After the flask was purged with argon and sealed, the reaction mixture was stirred vigorously at room temperature for 48 h. Upon evaporation of the solvent the resulting crude product was dissolved in 70% aqueous acetic acid (10 mL) and heated under reflux at 80° C. for 40 min. After cooling to room temperature the reaction mixture was further acidified with 3N aqueous HCl (5 mL) and extracted with diethyl ether (3×20 mL). Evaporation of the aqueous layer gave a solid, which was washed with dichloromethane and dried to give (±)-α-phenylglycine hydrochloride (233 mg, 62% yield). $^1$H-NMR (250 MHz, methanol-$d_4$) δ 7.41–7.51 (br, 5H), 5.18 (s, 1H); $^{13}$C-NMR (63 MHz, methanol-$d_4$) δ 170.7, 131.0, 130.5, 129.7, 129.1, 57.6; HRMS-CI calcd for $C_8H_9NO_2$ (M$^+$+1) 152.0633, obsd 152.0591.

Example 14

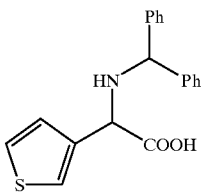

Preparation of (±)-N-(Diphenylmethyl)-α-(3-thienyl)glycine:

Prepared in 92% yield. $^1$H-NMR (360 MHz, DMSO-$d_6$) δ 7.20–7.75 (m, 13 H), 4.77 (s, 1H), 4.15 (s, 1H); $^{13}$C-NMR (90 MHz, DMSO-$d_6$) δ 173.3, 143.6, 143.2, 139.2, 122.7, 128.4, 127.1, 127.0, 126.8, 126.3, 64.1, 58.7.

Example 15

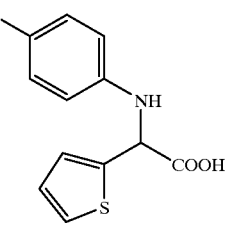

Preparation of (±)-N-(p-Anisyl)-α-(2-thienyl)glycine.

Prepared in ethanol over 12 h (79% yield). $^1$H-NMR (250 MHz, DMSO-$d_6$) δ 7.42 (d, J=5.2 Hz, 1H), 7.17 (d, J=3.5 Hz, 1H), 6.98 (dd, J=5.2 Hz, J=3.5 Hz, 1H), 6.65 (br, 4H), 5.29 (s, 1H), 3.61 (s, 3H); $^{13}$C-NMR (63 MHz, DMSO-$d_6$) δ 172.7, 151.9, 142.4, 141.2, 127.1, 126.2, 125.8, 114.8, 114.7, 56.9, 55.5.

Example 16

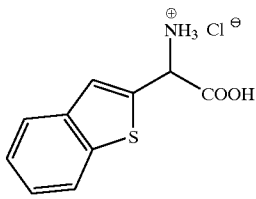

Preparation of (±)-N-α-(2-benzo[b]thienyl) glycine hydrochloride.

Prepared in dichloromethane over 12 hours (80% yield). $^1$H NMR (360 MHz, DMSO-$d_6$) δ 7.35–8.21 (m, 5H), 5.55 (s, 1H); $^{13}$C NMR (90 MHz, DMSO-$d_6$) δ 168.6, 139.4, 138.5, 135.2, 125.6, 125.4, 125.0, 124.2, 122.7, 51.7; HRMS-CI calcd for $C_{10}H_9NO_2S$ (M$^+$+1) 208.0354, obsd 208.0387.

Example 17

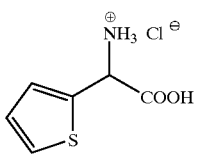

Preparation of (±)-N-α-(2-thienyl)glycine hydrochloride.

Prepared in dichloromethane over 12 hours (79% yield). $^1$H-NMR (360 MHz, DCl/D$_2$O) δ 6.48 (d, J=4.8 Hz, 1H), 6.21 (d, J=3.7 Hz, 1H), 5.99 (dd, J=4.8 Hz, J=3.7 Hz, 1H), 4.50 (s, 1H); $^{13}$C-NMR (90 MHz, DCl/D$_2$O) δ 169.9, 131.6, 130.5, 129.8, 128.4, 52.0; HRMS-CI calcd for C$_6$H$_7$NO$_2$S (M$^+$+1) 158.0197, obsd 158.0199.

Example 18

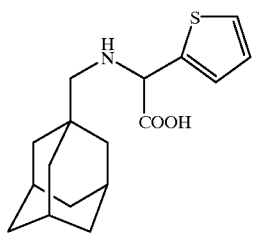

Reaction was run similarly to example 6, for 12 hours in dichloromethane, 90% yield. $^1$H NMR (360 MHz, DMSO-d$_6$) δ 7.46 (d, J=4.8 Hz, 1H), 7.15 (d, J=3.2 Hz, 1H), 7.00 (dd, J=4.8 Hz, 3.2 Hz, 1H), 4.52 (s, 1H), 1.31–2.52 (m, 17H). $^{13}$C NMR (90 MHz, DMSO-d$_6$) δ 170.2, 126.8, 126.7, 126.3, 126.0, 61.3, 58.6, 39.6, 36.4, 32.6, 27.6.

Example 19

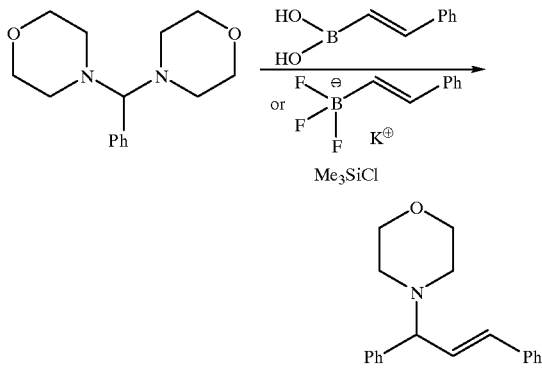

Preparation of 1-morpholino-1.3-diphenyl-2-propene.

The synthesis of substituted allylamines cannot be accomplished by the simple mixing of an aldehyde or ketone with an amine and a boronic acid. The reaction is also slow with aminals or preformed iminium salts. However, aminals can react in the presence of boron trifluoride to give the expected products. In another variation, the boronic acid can be reacted with potassium hydrogen fluoride to give the corresponding trifluoroborate salt, which can react readily with aminals in the presence of trimethylsilyl chloride.

To a vigorously stirred solution of (E)-2-phenylethenyl boronic acid (200 mg, 1.351 mmol) in methanol (10 mL) was slowly added excess saturated potassium hydrogen fluoride (15 mL, of a 4.5 M solution). After 15 min, the precipitated product was collected and washed with cold methanol. Recrystallization from minimal acetonitrile produced pure (E)-2-phenylethenyl-trifluoroborate (229 mg, 81% yield). $^1$H-NMR (360 MHz, d$_3$-acetonitrile) δ 7.1–7.4 (m, 5H), 6.6 (d, J=18.8 Hz, 1H), 6.28 (dq, J=18.8 Hz, 4.1 Hz, 1H).

Alternative procedure: To a suspension of (E)-2-phenylethenyltrifluoroborate (100 mg, 0.476 mmol) and 4,4'-benzylidenedimorpholine (124 mg, 0.473 mmol) in dry tetrahydrofuran (10 mL) stirred under nitrogen at room temperature was added chlorotrimethylsilane (102 mg, 0.940 mmol). After stirring at room temperature for 6 hours the reaction was heated at 50° C. for 3 hours and the mixture was poured into brine (50 mL), extracted with ether (3×50 mL), and the combined organic layers were dried over magnesium sulfate. Product purification by flash column chromatography (silica,1:4 ethyl acetate/hexanes) afforded pure 1-morpholine-1,3-diphenyl-2-propene as a colorless oil (90 mg, 68% yield). $^1$H-NMR (250 MHz, d6-acetone) δ 7.2–7.5 (m, 10H), 6.65 (d, J=15.7Hz, 1H), 6.36 (dd, J=15.7Hz, 8.8Hz, 1H), 3.84 (d, J=8.8 Hz, 1H), 3.65 (t, J=6.8Hz, 4H), 2.45 (t, J=6.8 Hz, 4H).

Example 20

A variation that does not require any additives is the reaction of organoboronic acids with nitrones which gives smoothly the corresponding product:

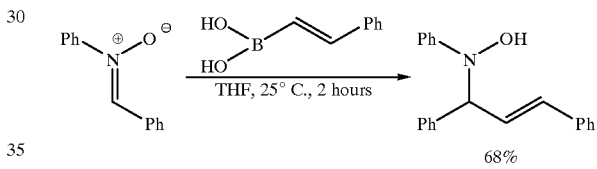

A typical experimental procedure was as follows: To a stirred solution of N-α-diphenyl nitrone (115 mg, 0.584 mmol) in tetrahydrofuran (7 mL) was added (E)-2-phenylethenyl boronic acid (86 mg, 0.584 mmol) and the reaction mixture was stirred in the dark at room temperature for 5 hours. After this time the mixture was poured into brine (50 mL), extracted with ether (3×50 mL) and the combined organic layers were dried over magnesium sulfate. Product purification by flash column chromatography (silica, 3:7 ethyl acetate/hexanes) afforded pure 1-(N-hydroxy-N-phenyl)-1,3-diphenyl-2-propene (120 mg, 68% yield). $^1$H-NMR (250 MHz, d$_6$-benzene) δ 6.82–7.5 (m, 15H), 6.75 (dd, J=16.1 Hz, J=7.8 Hz, 1H), 6.36 (d, J=16.1 Hz, 1H), 5.13 (d, J=7.8 Hz, 1H).

Example 21

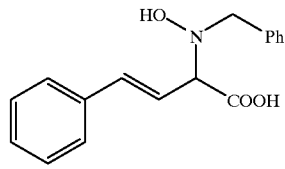

Following the procedure of example 20, the reaction was run for 16 hours in MeOH, 82% yield. $^1$H NMR (360 MHz, DMSO-d$_6$) δ 7.18–7.51 (m, 10H), 6.71 (d, J=15.9 Hz, 1H), 6.37 (dd, J=15.9 Hz, 9.1 Hz, 1H), 4.02 (d, J=9.1 Hz, 1H), 3.91 (d, J=13.8 Hz, 1H), 3.67 (d, J=13.8 Hz, 1H). $^{13}$C NMR (63 MHz, DMSO-$d_6$) δ 171.6, 138.4, 136.1, 134.3, 129.2, 128.7, 128.0, 127.9, 126.7, 126.5, 124.6, 74.1, 60.7.

Example 22

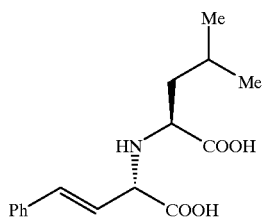

A mixture of L-leucine (100 mg, 0.762 mmol), glyoxylic acid monohydrate (70 mg, 0.762 mmol) and (E)-2-phenylethenyl boronic acid (113 mg, 0.764 mmol) in water (8 mL) was stirred vigorously for 24 hours at 50 C. The precipitate was isolated by filtration, washed with methanol (10 mL) and dried under vacuum to give (E)-2-[(S)-N-(-1'-carboxy-3'-methylbutyl)-amino-4-phenyl-3-butenoic acid (247 mg, 85% yield, 94% de). $^1$H-NMR (360 MHz, $d_6$-DMSO) δ 7.2–7.5 (m, 5H), 6.62 (d, J=15.3 Hz, 1H), 6.18 (dd, J=15.3 Hz, 8.1 Hz, 1H), 3.82 (d, J=8.1 Hz, 1H), 3.32 (m, 1H), 1.7 (m, 2H), 1.4 (m, 1H), 0.85 (d, 6.8 Hz, 6H).

Example 23

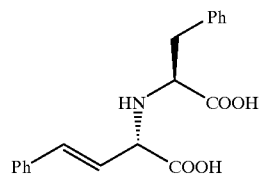

A mixture of L-phenylalanine (100 mg, 0.606 mmol), glyoxylic acid monohydrate (56 mg, 0.608 mmol) and (E)-2-phenylethenyl boronic acid (89 mg, 0.601 mmol) in methanol (8 mL) was stirred vigorously for 24 hours. The precipitate was isolated by filtration, washed with methanol (10 mL) and dried under vacuum to give (E)-2-[(S)-N-(1'-carboxy-2'phenyl)-amino-4-phenyl-3-butenoic acid (160 mg, 82% yield, 99% de). $^1$H NMR (360 MHz, DMSO-$d_6$) δ 7.18–7.45 (m, 10H), 6.58 (d, J=16.0 Hz, 1H), 6.10 (dd, J=16.0 Hz, 8.1 Hz, 1H), 3.91 (d, J=7.8 Hz, 1H), 3.45 (t, J=6.4 Hz, 1H), 2.88 (m, 2H). $^{13}$C NMR (90 MHz, DMSO-$d_6$) δ 174.9, 172.9, 138.0, 137.8, 136.1, 132.6, 129.4, 128.6, 127.7, 126.8, 126.4, 126.3, 61.7, 61.0, 59.6.

Example 24

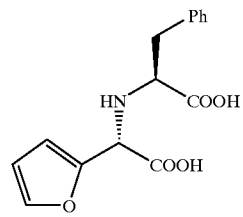

Prepared similarly to example 23, except that 2-furly boronic acid was used instead of (E)-2-phenylethenyl boronic acid. The reaction was run for 36 hours in methanol to give 59% yield. $^1$H NMR (360 MHz, DMSO-$d_6$) δ 7.21–7.65 (m, 6H), 6.37–6.47 (m, 2H), 4.42 (s, 1H), 3.39 (t, J=6.3 Hz, 1H), 3.16 (s, 1H), 2.87 (m, 2H). $^{13}$C NMR (90 MHz, DMSO-$d_6$) δ 174.0, 171.1, 151.3, 142.7, 137.7, 129.2, 128.0, 126.2, 110.4, 108.2, 59.2, 56.8, 38.1.

Example 25

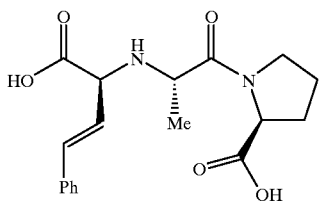

Alanine-proline (1,000 mg, 5.37 mmol), glyoxylic acid monohydrate (544 mg, 5.91 mml) and 2-phenylethenyl boronic acid (1,192 mg, 8 mmol) were vigorously stirred together in water (7 mL) for 48 hours. The precipitate was filtered, washed with acetone (2×10 mL) and dried to give a single crystalline product (1,488 mg, 80% yield, >99% de) the structure of which was confirmed with X-ray crystallography. $^1$H NMR (360 MHz, DCl/D$_2$O) δ 7.10–7.25 (br, 5H), 6.92 (d, J=15.6 Hz, 1H), 5.78 (dd, J=15.6 Hz, 9.8 Hz, 1H), 4.75 (d, J=9.8 Hz, 1H), 4.15 (q, J=6.8 Hz, 1H), 3.84 (m, 1H), 3.20 (m, 2H), 1.58 (m, 2H), 1.41 (d, J=6.8 Hz, 3H), 1.01–1.35 (m, 2H). $^{13}$C NMR (90 MHz, DCl/D$_2$O) δ 174.2, 168.7, 168.2, 142.6, 133.4, 130.4, 129.3, 127.1, 114.7, 62.3, 59.4, 54.0, 47.4, 28.0, 24.0, 15.1. HRMS-CI calcd for $C_{18}H_{22}N_2O_5$ (M+H$^+$) 347.1528, found 347.1598. Anal. Calcd for $C_{18}H_{22}N_2O_5$: C, 62.42; H, 6.40; N, 8.09. Found: C, 62.46; H, 6.41 N, 8.02. This compound was hydrogenated in methanol with Pd/C as catalyst to give pure enalaprilat.

Example 26

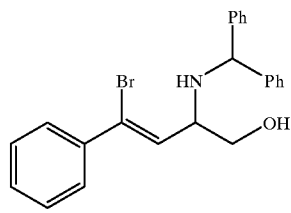

To the suspension of glycolaldehyde dimer (43 mg, 0.36 mmol) in toluene (7 mL) was added aminodiphenylmethane ( 132 mg, 0.72 mmol), followed by (E)-2-phenylethenyl boronic acid (164 mg, 0.72 mmol). The reaction flask was sealed and stirred vigorously for 24 hours at ambient temperature. After the evaporation of volatiles, the product was isolated by flash column chromatography on silica gel using ethylacetate-hexanes (3:7) as the eluent to give 247 mg of product, 84% yield. $^1$H NMR (250 MHz, CDCl$_3$) δ 7.21–7.55 (m, 15H), 6.10 (d, J=8.4 Hz, 1H), 5.03 (s, 1H), 3.88 (m, 1H), 3.72 (dd, J=10.8 Hz, 4.2 Hz, 1H), 3.51 (dd, J=10.8 Hz, 8.0 Hz, 1H).

$^{13}$C NMR (90 MHz, CDCl$_3$) δ 144.1, 142.9, 139.1, 130.9, 128.9, 128.6, 128.3, 127.6, 127.2, 64.6, 63.8, 60.1.

HRMS-CI calcd for $C_{23}H_{22}BrNO$ (M+H$^+$) 408.0884, found 408.0949.

Example 27

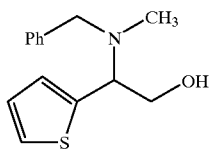

Synthesis performed as in example 35, except that ethanol was used as a reaction solvent. 77% yield.

$^1$H NMR (250 MHz, CDCl$_3$) δ 6.81–7.41 (m, 8H), 4.18 (dd, J=10.0 Hz, J=4.9 Hz, 1H), 3.94 (t, J=10.6 Hz, 1H), 3.67 (m, 1H), 3.65 (d, J=12.7 Hz, 1H), 3.41 (d, J=12.7 Hz, 1H), 2.21 (s, 3H).

$^{13}$C NMR (90 MHz, CDCl$_3$) δ 138.6, 137.1, 128.9, 128.4, 127.3, 126.6, 126.4, 124.8, 62.6, 61.3, 58.3, 36.5.

HRMS-CI calcd for C$_{14}$H$_{17}$NOS (M+H$^+$) 248.1031, found 248.1114.

Example 28

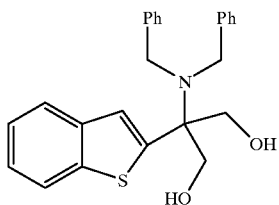

To the suspension of dihydroxyacetone (90 mg, 1 mmol) in ethyl alcohol (7 mL) was added dibenzylamine (197 mg, 1 mmol), followed by benzo[b]thiophene-2-boronic acid (178 mg, 1 mmol). Reaction mixture was stirred vigorously for 6 hours at ambient temperature. Precipitated product was isolated by filtration, washed with cold ethyl alcohol (2×10 mL) and dried. Obtained 250 mg of product, 62% yield. $^1$H NMR (360 MHz, acetone-d$_6$) δ 7.01–8.00 (m, 15H), 4.73 (d, J=11.4 Hz, 2H), 4.47 (d, J=11.4 Hz, 2H), 3.92 (s, 4H).

$^{13}$C NMR (90 MHz, acetone-d$_6$) δ 144.4, 140.3, 139.9, 134.1, 129.4, 128.7, 127.4, 126.0, 125.6, 125.3, 125.1, 124.9, 124.6, 124.1, 123.2, 123.1, 68.6, 63.9, 54.7. HRMS-CI calcd for C$_{25}$H$_{25}$NO$_2$S (M+H$^+$) 404.1606, found 404.1684.

Example 29

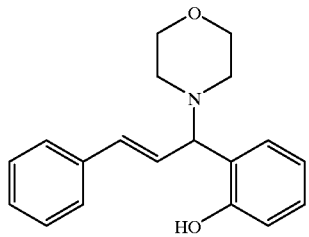

To the solution of salicylaldehyde (122 mg, 1 mmol) in ethyl alcohol (7 mL) was added morpholine (87 mg, 1 mmol), followed by (E)-2-phenylethenyl boronic acid (148 mg, 1 mmol). The reaction flask was sealed and stirred vigorously for 24 hours at ambient temperature. After the evaporation of volatiles, the product was isolated by flash column chromatography on silicagel using ethylacetate-hexanes (2:8) as the eluent. Obtained 260 mg of product, 88% yield. $^1$H NMR (360 MHz, acetone-d$_6$) δ 7.12–7.91 (m, 7H), 6.75 (m, 2H), 6.74 (d, J=15.9 Hz, 1H), 6.46 (dd, J=15.9 Hz, 9.5 Hz, 1H), 4.18 (d, J=9.5 Hz, 1H), 3.69 (t, J=5.0 Hz, 4H), 2.82 (s, 1H), 2.60 (br, 4H). $^{13}$C NMR (90 MHz, benzene-d$_6$) δ 157.5, 136.6, 134.0, 129.4, 129.1, 128.8, 128.1, 126.9, 126.7, 124.6, 119.8, 117.3, 74.4, 66.8, 51.4. HRMS-CI calcd for C$_{19}$H$_{21}$NO$_2$ (M+H$^+$) 296.1572, found 296.1648.

Example 30

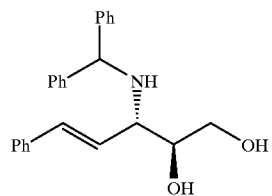

(D)-Glyceraldehyde (520 mg, ca. 75% in water, ca. 4.33 mmol) was dissolved in EtOH (15 mL) and to this solution was added aminodiphenylmethane (793 mg, 4.33 mmol), followed by (E)-2-phenylethenyl boronic acid (652 mg, 4.4 mmol). The reaction flask was sealed with plastic stopper and reaction mixture was vigorously stirred for 24 hours at ambient temperature. After the removal of volatiles, the residue was suspended in 6 N hydrochloric acid (20 mL) and heated with vigorous stirring at 60 C for 1 hour. After that time, the solution was cooled and filtered. The precipitate on the filter was washed with cold water (2×10 mL), ethylacetate (3×20 mL) and dried. Obtained 1201 mg of pure product (77% yield, >99% de). $^1$H NMR (250 MHz, CD$_3$OD) δ 7.30–7.65 (m, 15H), 6.60 (d, J=16 Hz, 1H), 6.33 (dd, J=16 Hz, 8.5 Hz, 1H), 5.59 (s, 1H), 4.18 (m, 1H), 3.93 (dd, J=8.5 Hz, 3.0 Hz, 1H), 3.57 (dd, J=10.9 Hz, 5.6 Hz, 1H), 3.40 (dd, J=10.9 Hz, 7.6 Hz, 1H). $^{13}$C NMR (63 MHz, C$_6$D$_6$) δ 144.8, 143.3, 137.1, 134.0, 129.0, 128.8, 128.7, 128.1, 127.9, 127.7, 127.4, 127.3, 126.8, 74.2, 65.2, 64.0, 61.5. HRMS-CI calcd. for C$_{24}$H$_{25}$NO$_2$ (M+H$^+$) 360.1885, found 360.1949.

Example 31

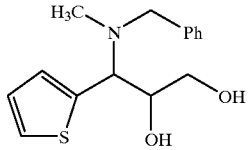

(DL)-Glyceraldehyde (100 mg, 1.11 mmol) was dissolved in EtOH (10 mL) and to this solution was added N-benzylmethylamine (134 mg, 1.11 mmol), followed by 2-thiophene boronic acid (143 mg, 1.12 mmol). The reaction flask was sealed with a plastic stopper and the reaction mixture was vigorously stirred for 24 hours at ambient temperature. After the removal of volatiles, the residue was redissolved in dichloromethane and purified by flash chromatography on silicagel using dichloromethane-methanol (800:70) as the eluent. Obtained 246 mg of pure product (80% yield, >99% de). $^1$H NMR (360 MHz, acetone-d$_6$) δ 7.12–7.49 (m, 8H), 4.20 (m, 1H), 3.92 (d, J=7.7 Hz, 1H), 3.65 (m, 2H), 3.61 (d, J=13.2 Hz, 1H), 3.40 (d, J=13.2 Hz, 1H), 2.14 (s, 3H).

$^{13}$C NMR (63 MHz, acetone-d$_6$) δ 140.2, 139.0, 129.6, 129.0, 128.0, 127.7, 126.9, 125.3, 72.3, 66.3, 66.1, 59.9, 38.4. HRMS-CI calcd. for C$_{15}$H$_{19}$NO$_2$S (M+H$^+$) 278.1136, found 278.1218.

Example 32

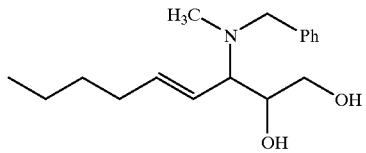

The reaction was performed as in example 31 in 73% yield, >99% de. $^1$H NMR (360 MHz, acetone-d$_6$) δ 7.25–7.35 (m, 5H), 5.69 (dt, J=15.4 Hz, 5.4 Hz, 1H), 5.47 (dd, J=15.4 Hz, 9.6 Hz, 1H), 3.84 (m, 1H), 3.68 (d, J=13.4 Hz, 1H), 3.60 (dd, J=10.7 Hz, 5.6 Hz, 1H), 3.51 (dd, J=10.7 Hz, 6.1 Hz, 1H), 3.43 (d, J=13.4 Hz, 1H), 2.90 (dd, J=9.6 Hz, 8.0 Hz, 1H), 2.18 (s, 3H), 2.05 (m, 2H), 1.8 (m, 4H), 0.9 (t, J=6.9 Hz, 3H). $^{13}$C NMR (63 MHz, acetone-d$_6$) δ 140.5, 137.3, 129.7, 129.0, 127.6, 125.5, 71.8, 69.6, 66.8, 59.7, 38.5, 33.0, 32.4, 22.8, 14.2. HRMS-CI calcd. for C$_{17}$H$_{27}$NO$_2$ (M+H$^+$) 278.2042, found 278.2031.

Example 33

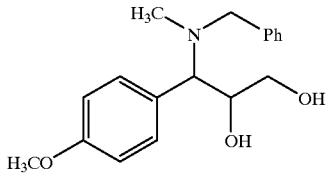

The reaction was performed as in example 31 in 72% yield, >99% de. $^1$H NMR (250 MHz, CDCl$_3$) δ 6.98–7.45 (m, 9H), 4.35 (m, 1H), 3.86 (s, 3H), 3.79 (d, J=5.7 Hz, 2H), 3.70 (d, J=9.4 Hz, 1H), 3.56 (d, J=13.1 Hz, 1H), 3.38 (d, J=13.1 Hz, 1H), 2.21 (s, 3H). $^{13}$C NMR (63 MHz, CDCl$_3$) δ 159.1, 138.2, 130.8, 128.9, 128.4, 127.2, 125.5, 113.6, 70.6, 68.4, 66.8, 59.4, 55.1, 37.9. HRMS-CI calcd. for C$_{18}$H$_{23}$NO$_3$ (M+H$^+$) 302.1678, found 302.1756.

Example 34

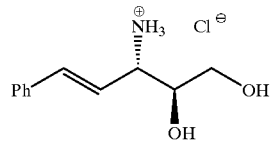

Prepared following examle 13, using di(p-anisyl)methyl amine followed by acid cleavage in 78% yield for 2 steps, >99% de and ee. $^1$H NMR (250 MHz, CD$_3$OD) δ 7.25–7.51 (m, 5H), 6.82 (d, 16.0 Hz, 1H), 6.30 (dd, J=16.0 Hz, 8.8 Hz, 1H), 4.08 (dd, J=8.8 Hz, 3.4 Hz, 1H), 3.92 (m, 1H), 3.58 (m, 2H). $^{13}$C NMR (63 MHz, CD$_3$OD) δ 138.7, 129.8, 129.7, 129.2, 127.9, 121.0, 72.2, 64.0, 57.4. HRMS-CI calcd. for C$_{11}$H$_{15}$NO$_2$ (M+H$^+$) 194.1103, found 194.1179.

Example 35

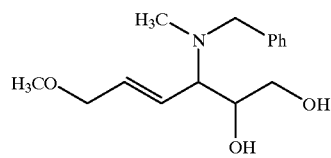

The product was obtained in 67% yield, >99% de. $^1$H NMR (250 MHz, acetone-d$_6$) δ 7.25–7.51 (m, 5H), 5.82 (ddt, J=15.3 Hz, 8.6 Hz, 1.3 Hz, 1H), 5.67 (dt, J=15.3 Hz, 5.5 Hz, 1H), 3.96 (dd, J=5.5 Hz, 1.3 Hz, 2H), 3.87 (m, 1H), 3.74 (d, J=13.3 Hz, 1H), 3.62 (dd, J=10.6 Hz, 5.5 Hz, 1H), 3.51 (dd, J=10.6 Hz, 6.2 Hz, 1H), 3.48 (d, J=13.3 Hz, 1H), 3.29 (s, 3H), 3.07 (dd, J=8.6 Hz, 7.5 Hz, 1H), 2.20 (s, 3H). $^{13}$C NMR (90 MHz, CDCl$_3$) δ 137.9, 134.5, 129.0, 128.6, 127.5, 125.7, 72.3, 69.4, 68.9, 66.5, 59.4, 58.2, 38.1. HRMS-CI calcd. for C$_{15}$H$_{23}$NO$_3$ (M+H$^+$) 266.1678, found 266.1764.

Example 36

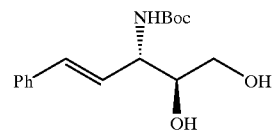

Prepared by protection with Boc$_2$O of the compound in example 34 in 89% yield, >99% de and ee. $^1$H NMR (360 MHz, CD$_3$OD) δ 7.18–7.41 (m, 5H), 6.58 (d, J=15.7 Hz, 1H), 6.27 (dd, J=15.7 Hz, 7.1 Hz, 1H), 4.27 (m, 1H), 3.68 (m, 1H), 3.58 (m, 2H), 1.45 (s, 9H). $^{13}$C NMR (90 MHz, CD$_3$OD) δ 157.8, 138.3, 133.1, 129.5, 128.5, 127.5, 127.4, 80.4, 75.2, 64.6, 56.1, 28.8. HRMS-CI calcd. for C$_{16}$H$_{23}$NO$_4$ (M+H$^+$) 294.1627, found 294.1705.

Example 37

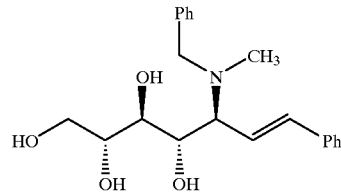

(D)-Ribose (158 mg, 1.05 mmol) was dissolved in EtOH (10 mL) and to this solution was added N-benzylmethylamine (127 mg, 1.05 mmol), followed by (E)-2-phenylethenyl boronic acid (163 mg, 1.1 mmol). The reaction flask was sealed with a plastic stopper and the reaction mixture was vigorously stirred for 24 hours at ambient temperature. After the removal of volatiles, the residue was redissolved in dichloromethane and purified by flash chromatography on silicagel using dichloromethane-methanol (600:50) as the eluent to obtain 278 mg of pure product (74% yield, >99% de). $^1$H NMR (360 MHz, CD$_3$OD) δ 7.20–7.45 (m, 10H), 6.61 (d, J=16.0 Hz, 1H), 6.33 (dd, J=16.0 Hz, 9.8 Hz, 1H), 3.98 (t, J=8.5 Hz, 1H), 3.65–3.88 (m, 5H), 3.58 (d, J=13.2 Hz, 1H), 3.49 (t, J=8.8 Hz, 1H), 2.25 (s, 3H). $^{13}$C NMR (90 MHz, CD$_3$OD) δ 138.9, 138.0, 137.8, 130.5, 129.6, 129.5, 128.8, 128.6, 127.6, 124.3, 77.2, 75.4, 71.4, 70.8, 64.1, 60.1, 37.9. HRMS-CI calcd. for C$_{21}$H$_{27}$NO$_4$ (M+H$^+$) 358.1940, found 358.1987.

Example 38

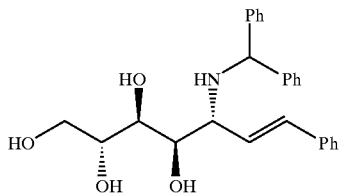

Prepared from (D)-Arabinose as in example 37 in 77% yield, >99% de. $^1$H NMR (360 MHz, CD$_3$OD) δ 7.20–7.43 (m, 15H), 6.34 (d, J=16.2 Hz, 1H), 6.20 (dd, J=16.2 Hz, 8.7 Hz, 1H), 4.98 (s, 1H), 3.88 (m, 2H), 3.77 (dd, J=11.4 Hz, 3.1 Hz, 1H), 3.68 (m, 1H), 3.63 (dd, J=11.4 Hz, 5.9 Hz, 1H), 3.45 (dd, J=8.7 Hz, 5.8 Hz, 1H). $^{13}$C NMR (90 MHz, CD$_3$OD) δ 138.3, 135.0, 129.6, 129.4, 128.9, 128.6, 128.4, 128.2, 128.0, 127.5, 73.2, 73.0, 72.9, 65.1, 64.7, 63.0. HRMS-CI calcd. for C$_{26}$H$_{29}$NO$_4$ (M+H$^+$) 420.2096, found 420.2155.

Example 39

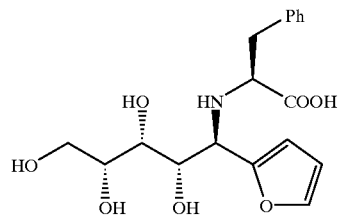

Prepared from (D)-Xylose as in example 37 except that 2-furyl boronic acid was used and the reaction was run for 48 hours in MeOH in 67% yield, >99% de. $^1$H NMR (360 MHz, CD$_3$OD) δ 7.55–7.60 (br, 1H), 7.21–7.38 (m, 5H), 6.43 (br, 2 H), 4.27 (m, 1H), 4.05 (m, 1H), 3.50–3.75 (m, 6H), 3.15 (m, 1H). $^{13}$C NMR (90 MHz, CD$_3$OD) δ 173.0, 145.3, 137.6, 130.6, 130.4, 130.0, 128.4, 113.5, 111.9, 72.9, 72.5, 71.6, 64.0, 63.0, 59.9, 37.0. HRMS-CI calcd. for C$_{18}$H$_{23}$NO$_7$ (M+H$^+$) 366.1474, found 366.1553.

Example 40

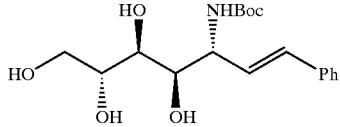

(D)-Arabinose (624 mg, 4.16 mmol) was dissolved in EtOH (15 mL) and to this solution was added 1,1-di-(p-anisyl)methylamine (1,012 mg, 4.16 mmol), followed by (E)-2-phenylethenyl boronic acid (670 mg, 4.53 mmol). The reaction flask was sealed with a plastic stopper and the reaction mixture was vigorously stirred for 24 hours at ambient temperature. Volatiles were removed under vacuum and the residue was heated with 80% acetic acid (10 mL) at 80° C. for 1 hour. Upon cooling, the reaction mixture was diluted with water (20 mL) and further acidified with 3 N hydrochloric acid (10 mL). After the extraction with diethyl ether (3×50 mL), water was evaporated and the resulting residue redissolved in methanol-triethylamine (10:1 by volume, 10 mL). To this solution was added di-tert-butyl dicarbonate (2,200 mg, 10 mmol) and the reaction mixture was heated at 45° C. for 40 min. After the removal of volatiles, pure product was isolated by flash column chromatography on silicagel using dichloromethane-methanol (850:150) as the eluent. Obtained 574 mg of pure product (39% yield for 3 steps, >99% de). $^1$H NMR (360 MHz, CD$_3$OD) δ 7.15–7.42 (m, 5H), 6.57 (d, J=15.9 Hz, 1H), 6.35 (dd, J=15.9 Hz, 5.6 Hz, 1H), 4.38 (m, 1H), 3.58–3.81 (m, 5H), 1.45 (S, 9H). $^{13}$C NMR (90 MHz, CD$_3$OD) δ 158.3, 138.5, 132.2, 129.5, 129.3, 128.4, 127.4, 80.5, 72.7, 72.5, 71.7, 65.0, 56.2, 28.8. HRMS-CI calcd. for C$_{18}$H$_{27}$NO$_6$ (M+H$^+$) 354.1838, found 354.1876.

Example 41

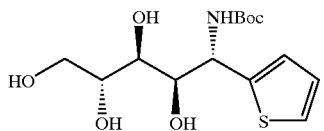

Prepared similarly to example 40 in 43% overall. $^1$H NMR (360 MHz, CD$_3$OD) δ 7.27 (dd, J=4.7 Hz, 1.0 Hz, 1H), 7.03 (d, 3.7 Hz, 1H), 6.96 (dd, J=4.7 Hz, 3.7 Hz, 1H), 5.05 (d, J=8.3 Hz, 1H), 4.07 (d, J=8.3 Hz, 1H), 3.58–3.81 (m, 4H), 1.43 (S, 9H). $^{13}$C NMR (90 MHz, CD$_3$OD) δ 157.9, 146.0, 127.6, 125.8, 125.1, 80.6, 72.8, 72.7, 71.4, 64.9, 54.5, 28.7. HRMS-CI calcd. for C$_{14}$H$_{23}$NO$_6$S (M+H$^+$) 334.1246, found 334.1324.

Example 42

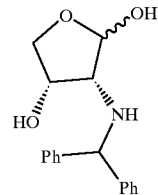

Obtained in 85% yield by ozonolysis of the compound in example 36 in methanol at −70 C for 5 min with subsequent methylsulfide workup. The crude product was purified by flash column chromatography on silicagel using dichloromethane-methanol (880:120) as the eluent. $^1$H NMR (360 MHz, DMSO-d$_6$) δ 7.15–7.48 (m, 10H), 5.81–6.09 (m, 1H), 4.95 (S, 1H), 4.89–5.13 (m, 2H), 4.08–4.18 (m, 1H), 3.77–3.91 (m, 1H), 3.58–3.74 (m, 1H), 3.35 (br, 2H), 2.74 (br, 1H). $^{13}$C NMR (90 MHz, DMSO-d$_6$) δ 144.8, 144.5, 144.3, 144.1, 128.4, 128.3, 128.2, 127.2, 127.0, 126.8, 126.7, 101.5, 95.1, 73.2, 72.4, 68.6, 67.4, 65.4, 64.4, 64.0, 60.5. HRMS-CI calcd. for C$_{17}$H$_{19}$NO$_3$ (M+H$^+$) 286.1365, found 286.1450.

Example 43

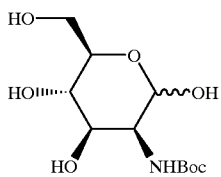

Obtained in 89% yield by ozonolysis of the compound in example 40, in methanol at −70° C. for 5 min with subsequent methylsulfide workup. The crude product purified by flash column chromatography on silicagel using dichloromethane-methanol (8:2) as the eluent.

$^{13}$C NMR (90 MHz, DMSO-$d_6$) δ 155.9, 155.7, 93.3, 93.0, 77.9, 77.5, 77.2, 72.7, 72.4, 68.3, 66.8, 66.5, 61.2, 60.9, 55.6, 55.2, 48.6, 28.3. HRMS-CI calcd. for $C_{11}H_{21}NO_7$ (M+H$^+$) 280.1318, found 280.1400

What is claimed:

1. A process for producing a compound of formula 1 comprising:

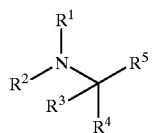

1 providing compounds of formula 13 and formula 14

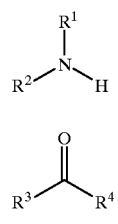

13

14 where R$^1$ and R$^2$ are each independently selected from the group consisting of hydrogen, alkyl, cycloalkyl, aryl, heteroaryl, acyl, acylalkyl, carboxy, carboxamido, trialkylsilyl, aryldialkylsilyl, diarylalkylsilyl, triarylsilyl, phosphinyl, and —YR, where Y is selected from the group consisting of —O—, —NR$_a$—, —S—, —SO—, and —SO$_2$—, and R and R$_a$ are each independently selected from the group consisting of hydrogen, alkyl, aryl, heteroaryl, and acyl, or R$^1$ and R$^2$ together form a bridge of 2 to 20 carbon atoms; and where R$^3$ and R$^4$ are each independently selected from the group consisting of hydrogen, carboxy, carboxamido, alkyl, cycloalkyl, aryl and heteroaryl, provided that the compound of formula 14 is not paraformaldehyde;

providing a compound of formula 15 or a compound of formula 19

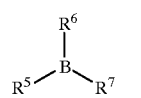

15

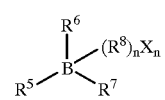

19 where R$^5$ is selected from the group consisting of alkyl, cycloalkyl, aryl, heteroaryl, alkenyl, alkynyl and allenyl; R$^6$, R$^7$ and R$^8$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms; X is a positive counter ion, and n is 0 or 1;

mixing said compounds of formula 13, formula 14, and formula 15 or 19 to form a reaction mixture; and allowing the reaction mixture to react to form the compound of formula 1.

2. The process of claim 1, wherein said reaction mixture further comprises a Lewis acid.

3. The process of claim 1, wherein R$^6$ and R$^7$ are each —OR.

4. The process of claim 3, wherein n is 1, R$^8$ is F, and said reaction mixture further comprises a compound of the formula SiR$^9$R$^{10}$R$^{11}$R$^{12}$, where R$^9$ is selected from the group consisting of halo, alkoxy, acyloxy, triflate, alkylsulfonate and arylsulfonate, and R$^{10}$, R$^{11}$, and R$^{12}$ are each independently selected from the group consisting of alkyl, cycloalkyl, aryl, alkoxy, aryloxy and chloro.

5. The process of claim 1, wherein R$^3$ is carboxy and the compound of formula 1 is an amino acid.

6. The process of claim 1, wherein R$^5$ is alkenyl.

7. The process of claim 1, wherein R$^3$ is acylalkyl and the compound of formula 1 is an α-amino carbonyl compound.

8. The process of claim 7, wherein R$^5$ is alkenyl.

9. The process of claim 1, wherein R$^3$ is selected from the group consisting of aminoalkyl, alkylamino-alkyl, dialkylamino-alkyl, and arylamino-alkyl and the compound of formula 1 is a 1,2-diamine.

10. The process of claim 1, wherein R$^3$ is hydroxyalkyl and the compound of formula 1 is an amino alcohol.

11. A process for generating a combinatorial library, said process comprising:

providing compounds of formula 13 and formula 14

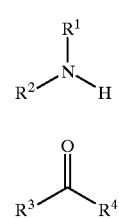

13

14 where R$^1$ and R$^2$ are each independently selected from the group consisting of hydrogen, alkyl, cycloalkyl, aryl, heteroaryl, acyl, acylalkyl, carboxy, carboxamido, trialkylsilyl, aryldialkylsilyl, diarylalkylsilyl, triarylsilyl, phosphinyl, and —YR, where Y is selected from the group consisting of —O—, —NR$_a$—, —S—, —SO—, and —SO$_2$—, and R and R$_a$ are each independently selected from the group consisting of hydrogen, alkyl, aryl, heteroaryl, and acyl, or R$^1$ and R$^2$ together form a bridge of 2 to 20 carbon atoms; and where R$^3$ and R$^4$ are each independently selected from the group consisting of hydrogen, carboxy, carboxamido, alkyl, cycloalkyl, aryl and heteroaryl provided that the compound of formula 14 is not paraformaldehyde;

providing a compound of formula 15 or a compound of formula

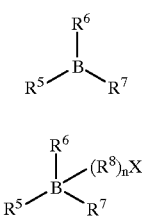

15

19

20 where R$^5$ is selected from the group consisting of alkyl, cycloalkyl, aryl, heteroaryl, alkenyl, alkynyl and allenyl; R$^6$, R$^7$ and R$^8$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms; X is a positive counter ion, and n is 0 or 1;

mixing said compounds of formula 13, formula 14, and formula 15 or 19 to form a reaction mixture; and allowing the reaction mixture to react to form the combinatorial library.

12. The process of claim 1, wherein:

the compounds of formula 13, formula 14 and formula 15 or 19 are mixed in a solvent selected from the group consisting of water, methanol, and ethanol, or a mixture thereof.

13. The process of claim 1, wherein:

the compounds of formula 13, formula 14 and formula 15 or 19 are mixed in the presence of air.

14. The process of claim 1, wherein:

the compounds of formula 13, formula 14 and formula 15 or 19 are mixed without heating.

15. The process of claim 1, wherein:

R$^3$ and R$^4$ are not both hydrogen.

16. The process of claim 1, wherein:

the compounds of formula 13, formula 14, and formula 15 or 19 are mixed to form a reaction mixture in a single step.

17. The process of claim 1, wherein:

the compound of formula 13 is an amino carbonyl compound and the compound of formula 1 is an N-acylalkylamino carbonyl compound.

18. The process of claim 1, wherein:

R$^3$ is hydroxyaryl and the compound of formula 1 is an amino phenol.

19. The process of claim 2, wherein n is 1.

20. The process of claim 1, wherein:

at least one of the compounds of formula 13, 14, 15 or 19 is chiral and the compound of formula 1 is produced stereoselectively.

21. The process of claim 11, wherein:

the compounds of formula 13, formula 14, and formula 15 or 19 are mixed to form a reaction mixture in a single step.

* * * * *